(12) United States Patent
Allcock et al.

(10) Patent No.: US 6,339,166 B1
(45) Date of Patent: Jan. 15, 2002

(54) PHOSPHINIMINE MODIFICATION OF ORGANIC POLYMERS AND SILICONES

(75) Inventors: Harry R. Allcock; Thomas J. Hartle; Michael B. McIntosh; Nicolas J. Sunderland; Robbyn Prange, all of State College; Jonathan P. Taylor, Lemont, all of PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/850,259

(22) Filed: May 7, 2001

Related U.S. Application Data

(63) Continuation of application No. 09/573,580, filed on May 18, 2000
(60) Provisional application No. 60/135,024, filed on May 20, 1999.

(51) Int. Cl.$^7$ .................................................. C07F 7/08
(52) U.S. Cl. ..................................................... 556/405
(58) Field of Search .......................... 556/405; 528/30; 526/193, 328, 344, 396, 348.7, 351, 352

(56) References Cited

U.S. PATENT DOCUMENTS 5,424,385 A * 6/1995 Hager et al. ............. 556/405 X
5,492,995 A * 2/1996 Englehardt et al. ....... 528/30 X

* cited by examiner

*Primary Examiner*—Paul F. Shaver
(74) *Attorney, Agent, or Firm*—Holland & Knight LLP

(57) ABSTRACT

Methods have been developed to produce phosphazene modified organic or siloxane polymers. The method includes (a) providing an organic or siloxane polymer comprising phosphine units, and (b) reacting the organic or siloxane polymer with a phosphazene azide compound under conditions wherein the phosphazene azide compound is bound to the phosphine unites in the polymer, thereby producing the phosphazene-modified organic or siloxane polymer. The organic polymer of step (a) is produced by reacting a first monomer comprising phosphine with a second monomer via free radical or anionic polymerization techniques to produce the organic polymer comprising phosphine units. The first and second monomers can be identical. A wide variety of organic polymer backbones can be modified using these techniques. The second monomer, for example, can be selected from monomers forming polyolefins, polydienes, polyacrylics, polyethylenes, polyvinyl chlorides, polyisoprenes, polystyrenes, polycaprolactam, poly(methyl) (meth)acrylates, and polypropylenes. Alternatively, the siloxane polymer of step (a) is produced by reacting a monomer comprising phosphine with a hydrosilicone polymer via hydrosilylation polymerization techniques to produce the siloxane polymer comprising phosphine units. These phosphazene modified organic and siloxane polymers are useful in a variety of applications, particularly as a fire retardant material.

30 Claims, 13 Drawing Sheets

PHOSPHINIMINE MODIFICATION OF ORGANIC POLYMERS AND SILICONES

CROSS-REFERENCE TO RELATED APPLICATIONS

This application is a continuation of pending prior application U.S. Ser. No. 09/573,580 filed May 18, 2000, which claims priority to U.S. Ser. No. 60/135,024, filed May 20, 1999.

STATEMENT REGARDING FEDERALLY SPONSORED RESEARCH

The government has certain rights in this invention by virtue of Grant Number 99-G-0013 awarded by the U.S. Federal Aviation Administration.

BACKGROUND OF THE INVENTION

The present invention generally relates to polymer compositions containing phosphorus-nitrogen units on non-polyphosphazene backbones and methods of manufacture thereof, which provide a more economical alternative to pure polyphosphazene polymers.

The incorporation of phosphorus-containing components into organic polymers is a subject of general interest because such systems offer the promise of fire retardance and enhanced thermal stability as well as resistance to oxidation by molecular oxygen (Kumar, et al., *Macromolecules*, 28:6323 (1995); Kumar, et al., *Macromolecules*, 16:1250 (1983)). Numerous methods have been explored to synthesize such hybrid macromolecules. For example, poly(vinylphosphine oxides) have been examined in some detail (Rabinowitz, et al., *J. Poly. Sci. Part A: Poly. Chem.*, 2:1233 (1964)). However, the linkage of phosphorus-nitrogen compounds to organic polymers offers some special advantages because of the synergistic fire retardance of phosphorus and nitrogen (Chamberlain in *Flame Retardancy of Polymeric Materials* (Kuryla & Papa, eds.), Vol. 4. (Marcel Dekker: New York, 1978)), and the overall stability under ambient conditions of species such as phosphazenes.

Small-molecule cyclic or linear phosphazenes can be incorporated into polymers in several ways. First, phosphazene rings may be linked through organic groups to yield cyclo-linear materials. These polymers incorporate a cyclic phosphazene trimer or tetramer directly into the backbone (Kumar, et al., *Macromolecules*, 28:6323 (1995); Kumar, et al., *Macromolecules*, 16:1250 (1983); Laszkiewicz, et al., Angew. *Makromol. Chem.*, 99:1 (1981); Kajiwara, *J. Macromol. Sci.-Chem.*, A16(2):587 (1981); Kajiwara, *Angew. Makromol. Chem.*, 37:141 (1974); Allcock, *Phosphorous-Nitrogen Compounds* (Academic Press: New York, 1972); Sharts, et al., *Inorg. Chem.* 5:2140 (1966); Bilbo, et al., *J. Poly. Sci. Part A; Poly. Chem.*, 5:2891 (1967); Tunca, et al. *J. Poly. Sci. Part A: Poly. Chem.*, 36:1227 (1988); Chen-Yang, et al., Phosphorous, *Sulfur, Silicon,* 76:261 (1993); Kumar, *J. Poly. Sci. Part A: Poly. Chem.*, 23:1661 (1985)). Of special interest are cyclo-linear species that are linked together via azide coupling reactions (Sharts, et al., *Inorg. Chem.*, 5:2140 (1966); Bilbo, et al., *J. Poly. Sci. Part A; Poly. Chem.*, 5:2891 (1967)). However, the difficulty involved in synthesizing high molecular weight polymers of this type, and the poor control of the molecular weight are major drawbacks. These problems can be solved by using a second approach, where vinyl or allyl compounds that bear cyclic phosphazene side groups are subjected to free radical addition polymerization or copolymerization to yield organic polymers with cyclophosphazene side groups (Allen, et al., *Macromolecules*, 21:2653 (1988)). In this case, the phosphazene ring is incorporated as a pendent side group rather than as part of the polymer backbone. Similar species have recently been prepared through the ring opening metathesis polymerization of norbornenes with cyclic phosphazene side units (Allcock, et al. *Macromolecules*, 32:7719 (1999)).

The incorporation of phosphorus atoms into organic polymers normally has the effect of decreasing their flammability (Green, *J. Fire Sciences*, 14:353–66 (1996)). Phosphazenes provide an excellent vehicle for the introduction of phosphorus into macromolecules. Cyclic phosphazene trimers have been incorporated into organic polymers in various ways. Researchers have demonstrated the homo- and copolymerization of cyclotriphosphazenes that bear an unsaturated side group via addition polymerization (Allen, *Trends Polym. Sci.*, 2:10, 342–49 (1994); Inoue, et al., *J. Polym. Sci. A: Polym. Chem.*, 30:145–48 (1992); Bosscher, et al., *J. Inorg. Organomet. Polym.*, 6:3, 255–65 (1996); Selveraj, et al., *Polymer*, 38:3617–23 (1997); Allcock. et al., *Macromolecules*, 32:7719–25 (1999)). Others have incorporated cyclic trimers into condensation polymers using difunctional species (Dez, et al., *Polym. Deg. Stab.*, 64:433–37 (1999); Tunca, et al., *J. Polym. Sci. A: Polym. Chem.*, 36:1227–32 (1998); Radhakrishnan Nair, et al., *Eur. Polym. J.* 32:1415–20; Chen-Yang, et al., *Phos. Sulf. Silicon.*, 76:261–64 (1993)). The drawback to both of these approaches is the need to study the polymerization behavior of each individual phosphazene monomer because the reactivity is affected both by the nature of the polymerizable group or groups and by the steric and electronic effects of the remaining side groups on the trimer.

It would be advantageous to provide improved methods for incorporating phosphorus-containing components into a range of organic polymers.

It is therefore an object of this invention to provide improved methods for incorporating phosphorus-containing components into a range of organic polymers.

It is another object of the present invention to provide a variety of phosphorus-containing organic polymers.

It is a further object of the present invention to provide phosphorus-containing organic polymers having improved fire retardant properties for use in a variety of applications.

It is still another object of the present invention to provide improved methods for incorporating phosphazenes into silicone polymers.

SUMMARY OF THE INVENTION

Methods have been developed to produce phosphazene modified organic or siloxane polymers. The method includes (a) providing an organic or siloxane polymer comprising phosphine units, and (b) reacting the organic or siloxane polymer with a phosphazene azide compound under conditions wherein the phosphazene azide compound is bound to the phosphine units in the polymer, thereby producing the phosphazene-modified organic or siloxane polymer. The organic polymer of step (a) is produced by reacting a first monomer comprising phosphine with a second monomer via free radical or anionic polymerization techniques to produce the organic polymer comprising phosphine units. The first and second monomers can be identical. A wide variety of organic polymer backbones can be modified using these techniques. The second monomer, for example, can be selected from monomers forming polyolefins, polydienes, polyacrylics, polyethylenes, polyvinyl chlorides, isoprenes, polystyrenes, polycaprolactam, poly(methyl methacrylate) and other poly-acrylates, and polypropylenes. Alternatively, the siloxane polymer of step (a) is produced by reacting a monomer comprising phosphine with a hydrosilicone polymer via hydrosilylation synthetic techniques to produce the siloxane polymer comprising phosphine units. These phosphazene modified organic and siloxane polymers are useful in a variety of applications, such as a fire retardant material, as demonstrated by the examples.

DETAILED DESCRIPTION OF THE INVENTION

Figure 1A:
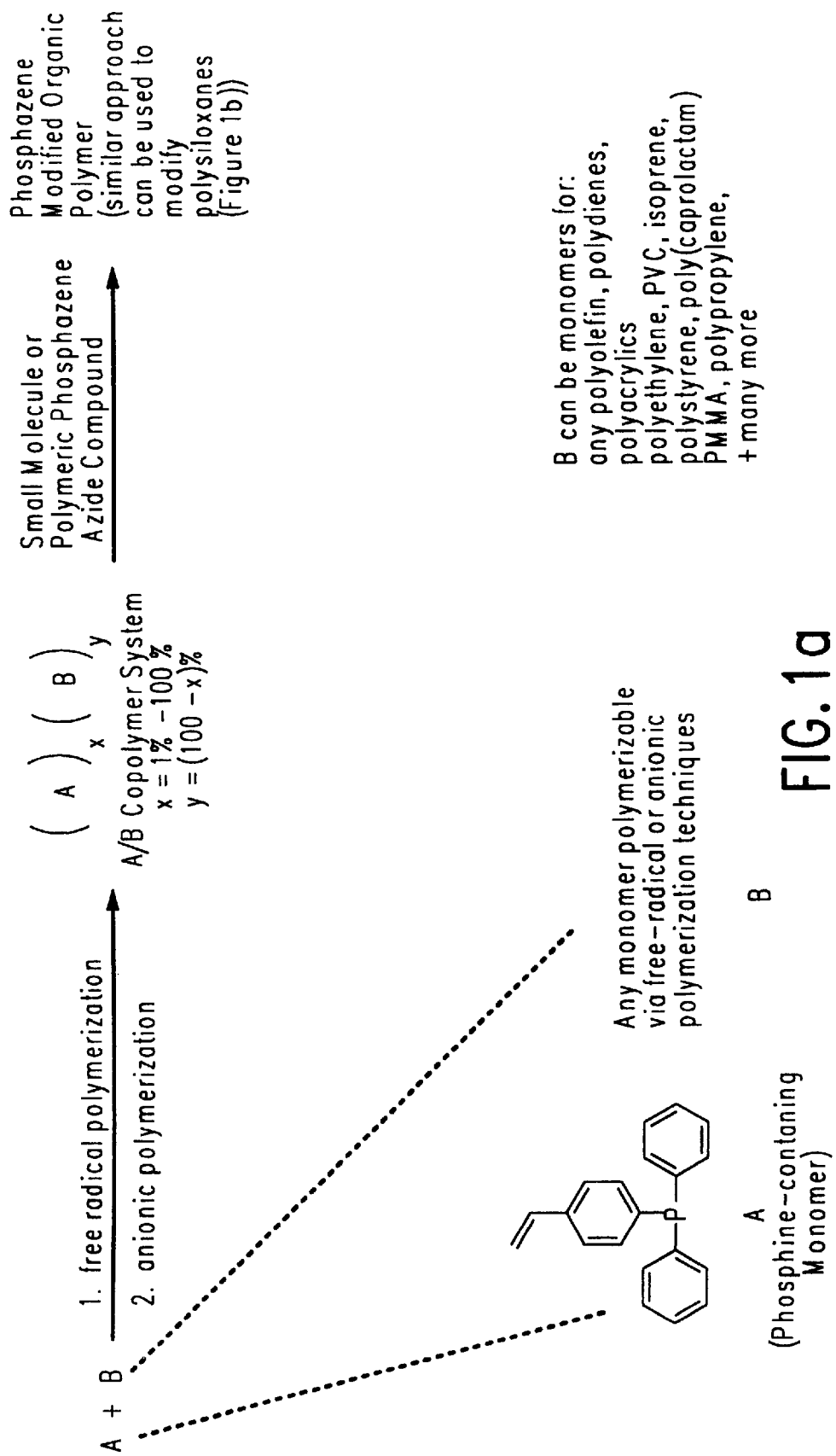
FIG. 1a shows the general reaction scheme of the presently disclosed phosphinimine modification method for organic polymer systems.

A relatively simple method has been developed for incorporating phosphorus-containing components into organic polymers and silicones to yield phosphazene modified organic polymers and silicones. Schemes for the method are shown generally in FIGS. 1a and 1b. First, a phosphine-containing monomer (A) is reacted with a second monomer (B) via a free radical or anionic polymerization technique (FIG. 1a), or the phosphine-containing monomer (A) is reacted with a hydrosilicone polymer (B') via a hydrosilylation synthetic technique (FIG. 1b), to produce a phosphine-modified polymer. Note that monomer B can be identical to monomer A in the free radical or anionic polymerization to yield homopolymer A. The phosphine-modified polymer then is reacted with a small molecule or polymeric phosphazene azide compound to yield a phosphazene-modified organic or siloxane polymer.

I. Reactant Monomers and Polymers

Monomer A

Monomer is a phosphine-containing monomer. Essentially any phosphine-containing unit that can be reacted with or otherwise incorporated into a polymer backbone. A preferred polymer is one that is polymerized via free radical or anionic polymerization or is susceptible to hydrosilylation. A preferred monomer is diphenyl-p-styrylphosphine.

These phosphine containing monomers can be made using techniques known in the art.

Monomer B

Monomer B is an organic monomer that can copolymerized with monomer A. Monomer B preferably is polymerizable via free radical or anionic polymerization techniques. The monomer can be any of several monomers, including but not limited to monomers for polyolefins, polydienes, polyacrylics, polyethylenes, polyvinyl chlorides, polyisoprenes, polystyrenes, polycaprolactam, poly(alkyl) (meth)acrylates (including polyacrylate and derivatives thereof as well as derivatives of polymethacrylate), and polypropylenes. Preferred polymer backbones are polystyrene and poly(methyl methacrylate).

Monomer B can be identical to monomer A, the phosphine-containing monomer, thus yielding a phosphine-containing homopolymer. For example, diphenyl-p -styrylphosphine can be polymerized to yield poly(diphenyl-p-styrylphosphine).

Generally, the specific copolymer produced depends on the types and relative amounts of starting monomers A and B.

Polymer B'

Polymer B' is a hydrosilicone polymer which undergoes hydrosilylation reaction with a monomer comprising phosphine. The hydrosilicone polymer preferably is a copolymer having the formula:

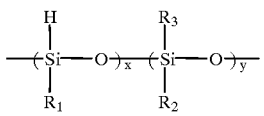

wherein $R_1$, $R_2$, and $R_3$ each are H or a linear, branched, or cyclic hydrocarbons, and wherein x is between 1% and 100%, and wherein y=(100−x)%. In one embodiment, the copolymer is (methylhydrosiloxane)-(dimethylsiloxane). Alternatively, the Si-H moiety can located at the termini of polymers, including but not limited to polysiloxanes.

These hydrosilicone polymer are commercially available or can be made using techniques known in the art.

Phosphazene Azide

In a preferred embodiment, the phosphazene azide is a cyclotriphosphazene having a single azido side group, which yields a polymer having trimeric phosphazene rings linked to every repeating unit containing a phosphine in the polymer backbone. The linkage is through a phosphinimine bond. Alternatively, cyclic tetrameric or linear phosphazene chains containing azido functionality are linked to the phosphine-containing polymers through the formation of a phosphinimine bond. Phosphazenes (linear or cyclic) containing multiple azide groups may be effective cross-linking agents for phosphine-containing polymers. These compounds containing multiple azide groups would cross-link phosphine-containing polymers via phosphinimine formation. Non-phosphazene azide compounds also can be used to modify phosphine-containing polymers. Diphenylphosphoryl azide is a representative phosphazene azide, which is used in the Examples below.

The phosphazene azides can be made using techniques known in the art.

II. Phosphazene Modified Organic and Siloxane Polymers

The polymer comprises a phosphine molecule bound covalently to a non-polyphosphazene backbone, typically an organic polymer or siloxane polymer. Any free radical or anionically polymerizable polymer can be modified to incorporate a small molecule phosphine, which is then used to add phosphazene pendent groups via a phosphazene azide. The mole percentage of phosphinated monomer in the polymer generally is between about 1% and 100%.

A phosphine-imine reaction then can be used to attach polyphosphazene side chains to the polymer backbone via the phosphine molecule which is covalently bound within the backbone. The azide on the phosphazene (small molecule or polymer) reacts with the phosphine molecule which is covalently bound to the non-phosphazene backbone.

The phosphazene azide species can be functionalized with a wide variety of organic side chains to help impart the desired properties to the end polymer system. The phosphazene azide may be hydrophilic or hydrophobic, rigid or flexible, and reactive or nonreactive. The extent to which phosphazene systems can be functionalized has been widely studied and is known in the art.

III. Method of Making the Phosphazene Modified Compositions

Figure 1B:
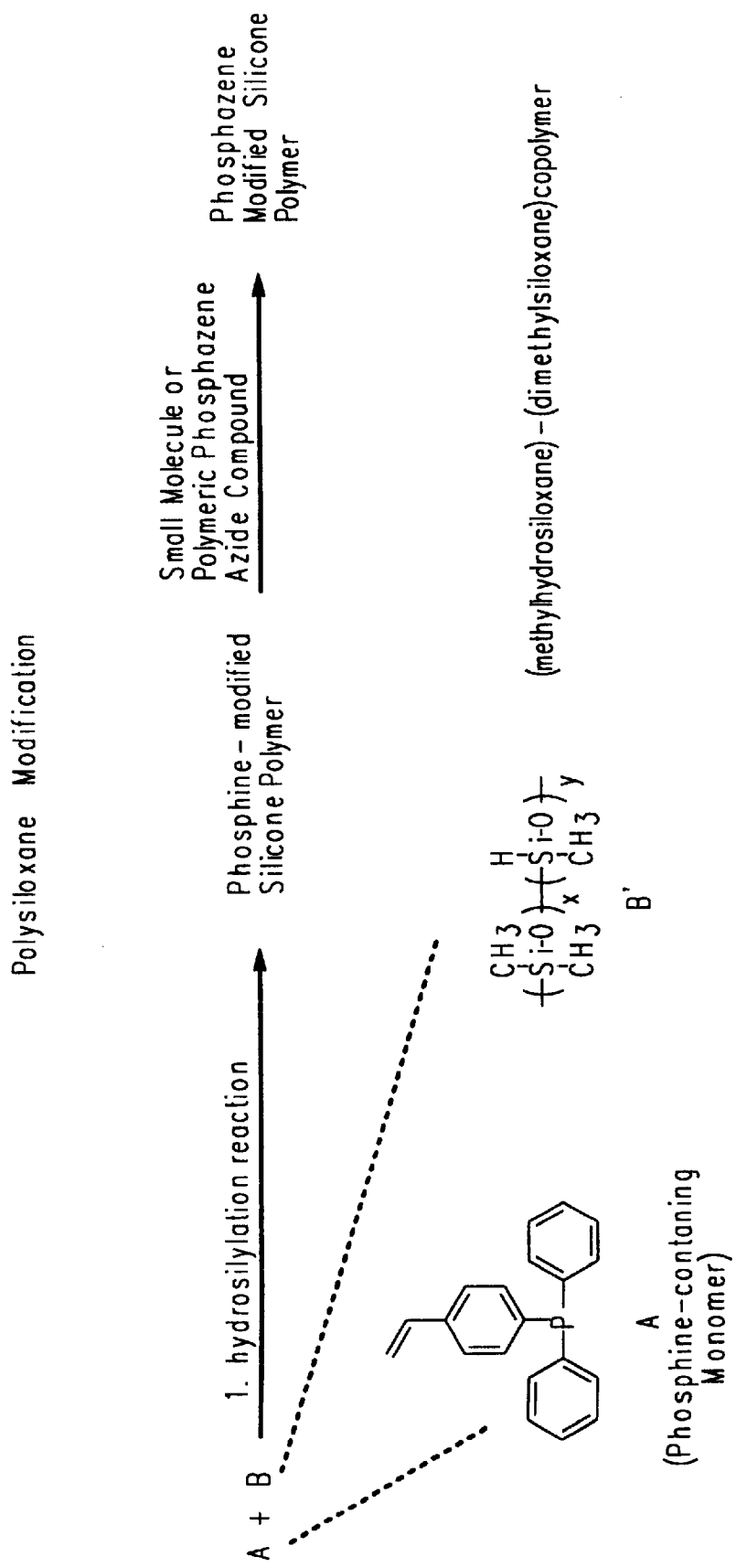
FIG. 1b shows the general reaction scheme of the presently disclosed phosphinimine modification method for polysiloxanes.

Schemes for the methods are shown generally in FIGS. 1a and 1b as described above.

In one embodiment, the method uses the Staudinger reaction to attach cyclic phosphazene trimers bearing azide groups to phosphorus (III) atoms pendent to the organic polymer backbone. A preferred embodiment uses diphenyl-p-styrylphosphine which can be polymerized by either anionic or free radical methods. The styrene-based phosphine-containing polymers are then treated with a variety of azido compounds such as $N_3P_3(OCH_2CF_3)_5(N_3)$, $N_3P_3(OC_6H_5)(N_3)$, and $(C_6H_5O)_2P(=O)(N_3)$ in near quantitative yields. A similar approach can be used to modify copolymers of diphenyl-p-styrylphosphine with both styrene and methyl methacrylate. This approach should be applicable to a wide variety of organic polymer systems.

Figure 2:
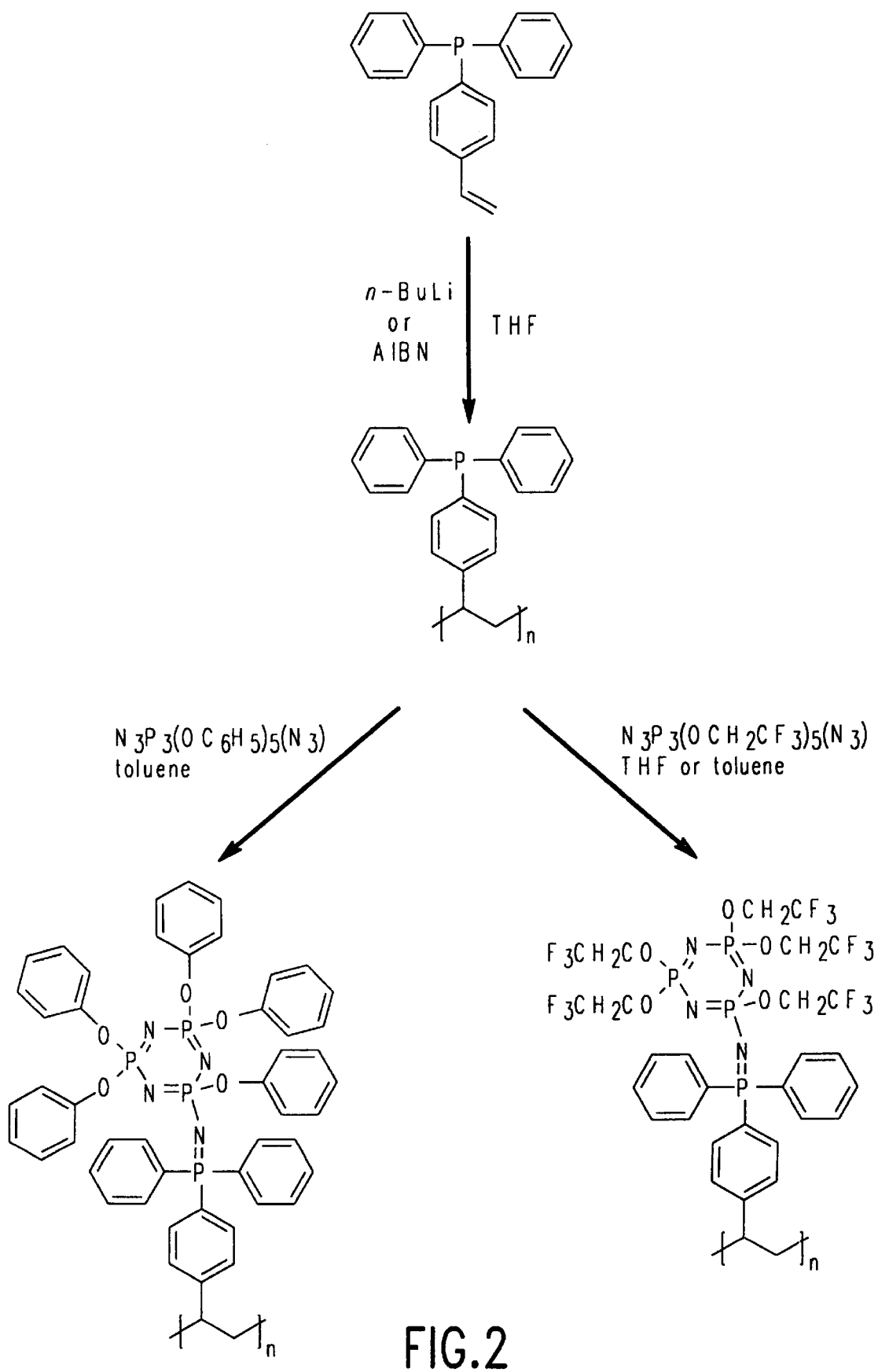
FIG. 2 shows a reaction scheme in which the cyclic phosphazene is coupled to the phosphinated styrene polymer through a P=N—P (phosphinimine) linkage.

As demonstrated by the examples, polystyrene with diphenylphosphine pendent units (polydiphenyl-p-styrylphosphine) was allowed to react with cyclic phosphazene azides. This process couples the cyclic phosphazene to the phosphinated polystyrene through a P=N—P (phosphinimine) linkage (see FIG. 2). Such reactions occur readily under mild conditions (McIntosh, et al., *J. Am. Chem. Soc.*, 121:884 (1998)).

Figure 3:
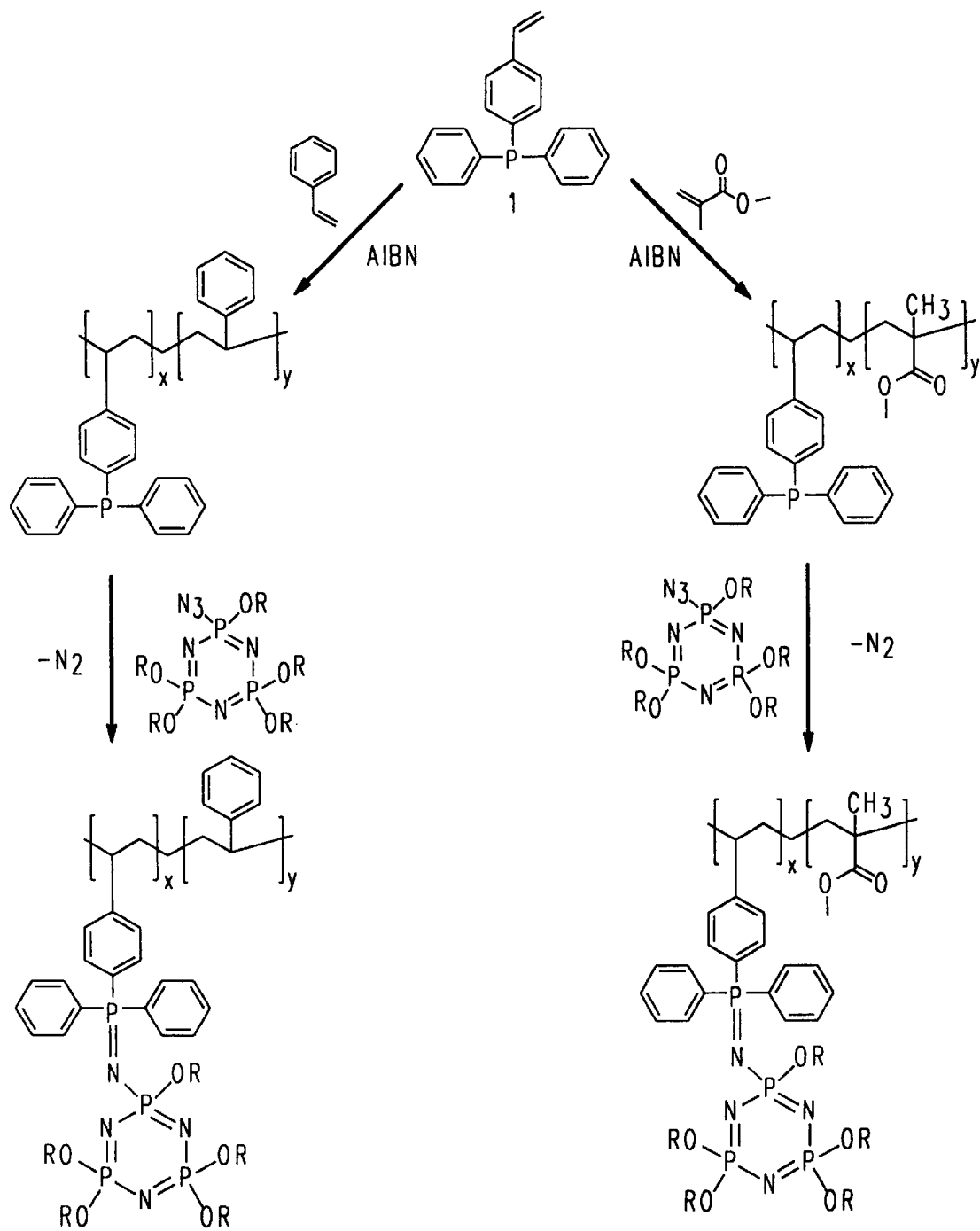
FIG. 3 shows a reaction scheme in which the azidophosphazenes is coupled with copolymers of diphenyl-p-styrylphosphine with styrene or methyl methacrylate.

Properties of the resultant polymers can be tailored by varying the nature of the phosphazene. Diphenyl-p-styrylphosphine polymerizes via anionic or free-radical methods (Rabinowitz, et al., *J. Poly. Sci. Part A: Poly. Chem.*, 2:1241 (1964)), which allows a wide variety of co-monomers to be used for property modification. Coupling reactions between the azidophosphazenes and copolymers of diphenyl-p-styrylphosphine with styrene or methyl methacrylate are described (FIG. 3) and phosphoryl units can be linked to the phosphinated polystyrene by treatment with diphenylphosphoryl azide.

In one embodiment, phosphazene cyclic trimers are incorporated into organic polymers. In this method, a preformed organic polymer, e.g., poly(diphenyl-p-styrylphosphine), is treated with cyclotriphosphazenes that bear a single azido side group. The product polymer has trimeric phosphazene rings linked to every repeating unit through a phosphinimine bond. A method to copolymerize diphenyl-p-styrylphosphine (1) with styrene or methyl methacrylate has been reported by Rabinowitz, et al., *J. Polym. Sci., Part A*, 2:1233–40 (1964); Rabinowitz, et al., *J. Polym. Sci., Part A*, 2:1241–49 (1964). It is possible to produce both random and block copolymers with controlled molecular weights and comonomer distributions. In addition, because 1 can be polymerized via either free radical or anionic addition techniques, a wide range of conventional monomers can copolymerize with it. The side groups on the phosphazene also can be varied to fine-tune the properties of the polymer, as described above).

The examples demonstrate forming copolymers from diphenyl-p-styrylphosphine and either styrene and methyl methacrylate using cyclophosphazene azides. The mole percentage of phosphinated styrene in the copolymer can, for example, be between about 1% and 99%. In some embodiments, the mole percentage preferably is between about 1% and 10%. The amount of phosphazene linked to each chain is controlled directly by the percentage of the functionalized styryl unit.

The ability of 1 to polymerize via both free-radical and anionic addition techniques allows control to be exercised over chain lengths and molecular weight distribution. The control afforded by anionic polymerizations is well known in the art. The incorporation of cyclic phosphazene trimers into organic polymers offers many advantages.

In another embodiment, cyclic phosphazene azides are incorporated into silicone polymers. For example, poly (dimethylsiloxane)-co-poly(hydromethylsiloxane) first can reacted with diphenyl-p-styrylphosphine via a hydrosilylation reaction. Then the resultant phosphine-containing silicone polymer can be reacted with a fluorinated cyclic phosphazene azide compound to yield a silicone polymer with phosphazene pendent side-groups. By varying the percentage of repeat units containing Si—H bonds, the percent of repeat units bearing phosphazenes in the final polymer can be controlled. Example 3 below describes preparation of a modified silicon polymer having phosphazene pendent groups present on roughly 18% of the polymer repeat units.

V. Applications for the Synthetic Methods and Polymer Compositions

The methods described above provide for the synthesis of flame retardant organic polymers, the surface modification of organic polymers, a means for cross-linking of organic polymers, the synthesis of phophazene/organic polymer interpenetrating networks, the synthesis of compatibilizing agents for polyphosphazene/organic polymer blends and copolymers, and the synthesis of materials for use as solid polymer electrolytes.

The polymer compositions can be used directly or incorporated into other materials for a wide variety of applications. In particular, the polymer compositions can be used to increase flame resistance of materials and objects formed of the materials (articles of manufacture). Complex phosphazene structures of interest in a range of industries, including but not limited to medicine and fuel cell and battery technologies, can be incorporated into a variety of organic polymers. Other uses for these polymer compositions include but are not limited to applications in medical implants and adhesives in electronics.

The compositions and methods described herein will be further understood with reference to the following non-limiting examples.

EXAMPLE 1

Preparation of Poly(diphenyl-p-styrylphosphine)

Overview

Poly(diphenyl-p-styrylphosphine) was synthesized by both anionic and free radical addition polymerization processes. n-Butyl lithium was employed as the initiator for the anionic polymerization in THF at −78° C. The reactions were complete within 0.5 hours. The polymers were deactivated by quenching with methanol and were allowed to warm to room temperature. The polymer was purified by multiple precipitations from THF into methanol and hexanes. The resultant white powder was dried under vacuum and was characterized by gel permeation chromatography (vs. polystyrene standards), elemental analysis, and multinuclear NMR ($^1$H, $^{31}$P, and $^{13}$C). The free radical polymerization of the same p-substituted styrene occurred readily in refluxing THF using AIBN as an initiator. The resultant polymer is similar to the one formed by the anionic polymerization route although, as expected, the polydisperity is slightly higher (2.33 vs. 1.69). Copolymers of diphenyl-p-styrylphosphine with both styrene and methyl methacrylate were synthesized using the free radical route and they were purified in a similar way.

Pendent cyclic phosphazene trimers were linked to the polymer by the addition of an excess of the appropriate phosphazene azide to a solution of the poly(diphenyl-p-styrylphosphine). Tetrahydrofuran, dioxane, and toluene were found to be suitable reaction solvents. The reactions were monitored by $^{31}$P NMR spectrometry. Complete conversion to the phosphinimine was generally detected within 72 hours at reflux. The resultant polymers were purified by multiple precipitations from THF into methanol and hexanes followed by Soxhlet extraction with hexanes for 48 hours. The identity of the while polymer was confirmed by multinuclear NMR and elemental analysis. Molecular weights were estimated by GPC relative to polystyrene standards. A similar approach was utilized for linkage of phosphoryl azides to the polymer backbone.

Instruments $^{31}$P and $^1$H spectra were recorded with use of a Bruker AMX-360 NMR operated at 146 and 360 MHz respectively. $^1$H NMR spectra are referenced to tetramethylsilane. $^{31}$P NMR chemical shifts are relative to 85% phosphoric acid as an external reference, with positive shift values downfield from the reference. The $^{31}$P NMR spectra were proton-decoupled.

Procedural Details

Diphenyl-p-styrylphosphine was synthesized following a method described in Rabinowitz, et al., *J. Org. Chem.*26:4157 (1961). The $N_3P_3(OC_6H_5)_5N_3$ and $N_3P_3(OC_2F_3)_5N_3$ were synthesized as described in McIntosh, et al., *J. Am. Chem. Soc.* 121:884 (1998).

(1) Anionic polymerization diphenyl-p-styrylphosphine

Diphenyl-p-styrylphosphine (1.00 g, 3.5×10$^{-3}$ mol) was dissolved in 20 mL of distilled THF and cooled to −78° C. Butyl lithium (2.5 M in hexane, 0.007 mL, 1.7×10$^{-5}$ mol) was added to the reaction flask via syringe. The reaction immediately changed from a clear, colorless solution to a clear, red solution. After stirring for 30 minutes at −78° C., 2 mL of methanol were added to quench the reaction. The reaction instantaneously changed from the red solution back to a clear colorless solution. The polymer was purified by multiple precipitations from THF into methanol (2×) and hexanes (2×). The resultant white powder was characterized by multinuclear NMR and gel permeation chromatography. $^{31}$P NMR (CD$_2$Cl$_2$) δ=6.3 (s, 1P); $^1$H NMR (CD$_2$Cl$_2$) δ=7.7–6.7 (bm, 12H), 6.5–6.1 (bs, 2H), 2.0–0.9 (bm, 3H).

(2) Free-radical polymerization of diphenyl-p-styrylphosphine

Diphenyl-p-styrylphosphine (1.0 g, 3.5 mol) and AIBN (1.4 mol %) were dissolved in distilled THF (20 mL) and stirred under argon. The reaction was heated to reflux for 12 hours. The polymer was purified in the same way as anionically polymerized phosphine polymer. The white polymer was indistinguishable from the anionically polymerized version via multinuclear NMR. $^{31}$P NMR (CD$_2$Cl$_2$) δ=6.3 (s, 1P); $^1$H NMR (CD$_2$Cl$_2$) δ=7.7–6.7 (bm, 12H), 6.5–6.1 (bs, 2H), 2.0–0.9 (bm, 3H).

(3) Reaction of $N_3P_3(OC_2F_3)N_3$ with poly(diphenyl-p-styrylphosphine)

Poly(diphenyl-p-styrylphosphine) (0.5 g, 1.7×10$^{-3}$ mol repeat units) and $N_3P_3(OC_2F_3)_5N_3$ (1.75 g, 2.6×10$^{-3}$ mol) were heated to reflux in toluene (100 mL) and stirred for 48 h. The polymer was purified by precipitations into hexanes (3×) followed by Soxhlet extraction with hexanes for 48 h. The resultant white polymer was characterized by multinuclear NMR, elemental analysis, and GPC. $^{31}$P NMR (THF-d8) δ=17.8 (d, 2P), 12.6 (bm. 1P), 11.1 (bm, 1P); $^1$H NMR (THF-d8) δ=8.0–7.1 (bm, 12H), 7.1–6.1 (bs, 2H), 4.7–4.4 (bs, 4H), 4.4–4.0 (bs, 6H), 2.1–0.9 (bm, 3H). Elemental analysis calculated for $C_{30}H_{27}F_{15}N_4O_5P_4$ (%); C, 38.62; H, 2.92; F, 30.57; N, 6.01; P, 13.29. Found C, 39.33: H, 2.82; F, 30.77; N, 5.84; P, 12.31.

(4) Reaction of $N_3P_3(OC_6H_5)_5N_3$ with poly(diphenyl-p-styrylphosphine) Poly(diphenyl-p-styrylphosphine) (0.5 g, 1.7×10$^{-3}$ mol repeat units) and $N_3P_3(OC_6H_5)_5N_3$ (1.67 g, 2.6×10$^{-3}$ mol) were heated to reflux in toluene (100 ml). The reaction was stirred for 72 h. The reaction mixture was concentrated and precipitated into methanol. The polymer was then precipitated from THF into hexanes (2×) followed by Soxhlet extraction with hexanes for 48 h. The resultant polymer was characterized by multinuclear NMR and gel permeation chromatography. $^{31}$P NMR (CD$_2$Cl$_2$) δ=11.3–9.7 (bs, 1P), 8.7–7.4 (overlapping bs, 2P), 7.4–5.7 (bm, 1P); $^1$H NMR (CD$_2$Cl$_2$) δ=7.6–5.7 (overlapping bm, 39H), 2.0–0.8 (bs, 3H).

(5) Reaction of diphenylphosphoryl azide with poly(diphenyl-p-styrylphosphine)

Poly(diphenyl-p-styrylphosphine) (0.5 g, 1.7×10$^{-3}$ mol repeat units) and diphenylphosphoryl azide (0.72 g, 2.6×10$^{-3}$ mol) were heated to reflux in toluene (100 mL) and stirred for 24 h. The polymer was purified by precipitations from chlorobenzene into diethyl ether (2×) followed by Soxhlet extraction with hexanes for 48 h. The resultant white polymer was characterized by multinuclear NMR and GPC. $^{31}$P NMR (CD$_2$Cl$_2$) 67 =13.6 (d, 1P), −7.4 (d, 1P); $^1$H NMR (CD$_2$Cl$_2$) δ=7.6–5.9 (overlapping bm, 24H), 2.2–0.7 (bs, 3H).

Results and Discussion

Figure 4A:
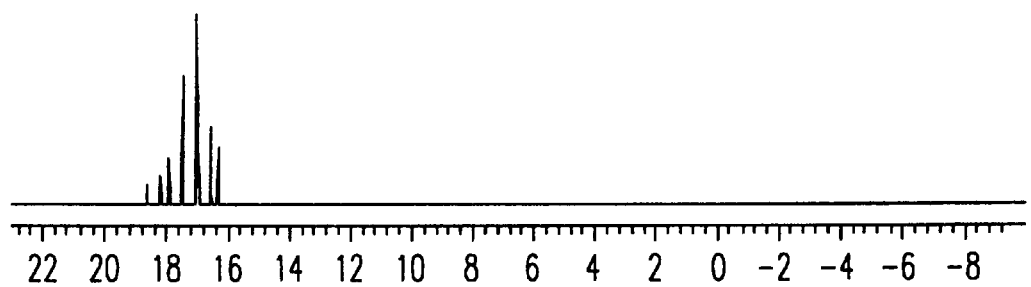
FIGS. 4a–4c show the $^{31}P$ NMR spectra of $N_3P_3(OCH_2CF_3)_5(N_3)$ (3a); polydiphenyl-p-styrylphosphine (3b), and phosphinimine modified product (3c) obtained from the reaction of polydiphenyl-p-styrylphosphine with $N_3P_3(OCH_2CF_3)_5(N_3)$.
Figure 4B:
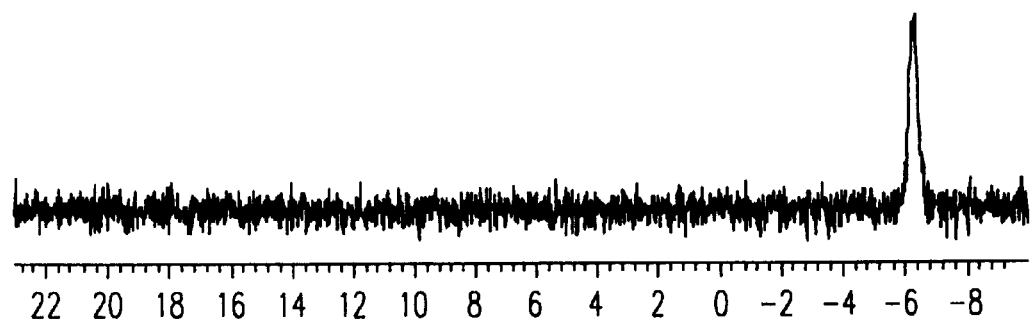
Figure 4C:
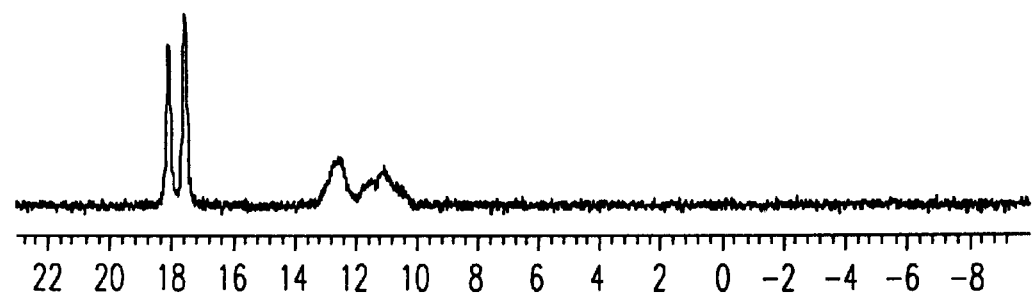

The linkage of the cyclophosphazene to the polystyrene appeared to be quantitative. Reactions were followed by $^{31}$P NMR to monitor their progress. Poly(diphenyl-p-styrylphosphine) generates a singlet peak near −6 ppm in $^{31}$P NMR spectra. Addition of the phosphazene azide causes this singlet to disappear, and a new peak corresponding to the phosphinimine to appear. The location of this new peak is dependent on the nature of the co-substituents on the cyclic phosphazene azide. Reactions were determined to be complete when the peak at −6 ppm could no longer be detected. This also is indicative of near quantitative conversion to the phosphinimine. A change in location of the chemical shift corresponding to the phosphorus within the phosphazene ring originally bound to the azide was also detected when either $N_3P_3(OC_6H_5)_5(N_3)$ or $N_3P_3(OCH_2CF_3)_5(N_3)$ reacted with the phosphinated polystyrene. FIG. 4 shows the $^{31}$P NMR spectra of the reactants and the purified product from the reaction of poly(diphenyl-p-styrylphosphine) with $N_3P_3(OCH_2CF_3)_5(N_3)$. Spectrum C is the final product. The phosphorus atom closest to the polymer backbone undergoes a shift from −6 ppm to 11 ppm. The phosphorous originally bound to the azide shifts from near 17 ppm to 13 ppm. These peaks are broad and their splitting is obscured due to their proximity to the polymer backbone. The two phosphorous atoms furthest from the reaction center remain near 17 ppm. A doublet is generated due to the splitting from the phosphorus originally bound to the azide. These chemical shifts are in good agreement with the results for small molecule analogs discussed in a previous work (Allcock, et al., *Inorg. Chem.*, 38:5535 (1999)). Integration of spectrum C is 1:1:2 moving downfield as expected for the repeat unit containing 4 phosphorus atoms. Starting materials were not detected by $^{31}$P NMR spectroscopy after purification. The purity of the final polymers was also verified by $^1$H NMR spectra and elemental analysis.

Further evidence for the coupling process comes from gel permeation chromatography results. Table 1 shows GPC derived data from a representative sample of poly(diphenyl-p-styrylphosphine) polymerized anionically as well as from products from the free radical initiated copolymerizations of diphenyl-p-styrylphosphine with both styrene and methyl-methacrylate. Date are also shown for the above polymers after treatment with the alkoxy and aryloxy phosphazene azides.

TABLE 1

GPC Analysis of Phosphinimine Modified Polymers

| | Initiator | $M_n$ | $M_w/M_n$ | Phosphazene Azide | $M_n$ | $M_w/M_n$ |
|---|---|---|---|---|---|---|
| Phosphine 1[a] | BuLi | 279000 | 1.66 | TFE | 2700000 | 1.54 |
| Phosphine 1[a] | BuLi | 279000 | 1.66 | Phenoxy | 965000 | 1.57 |
| Phosphine/styrene[b] | AIBN | 38900 | 1.66 | TFE | 54400 | 1.42 |
| Phosphine/styrene[b] | AIBN | 38900 | 1.66 | Phenoxy | 47500 | 1.61 |
| Phosphine/MMA[c] | AIBN | 142000 | 1.78 | TFE | 219000 | 1.77 |
| Phosphine/MMA[c] | AIBN | 142000 | 1.78 | Phenoxy | 339000 | 1.76 |

[a]poly(diphenyl-p-styrylphosphine)
[b]copolymer comprised of 10% diphenyl-p-styrylphosphine/90% styrene
[c]copolymer comprised of 20% diphenyl-p-styrylphosphine/80% methyl methacrylate In most instances, the $M_n$ of the polymer is increased dramatically after reaction with the phosphazene azide. However, the increase in molecular weight does not correspond to theoretical values for the modified polymers based on the molecular weights of the phosphine containing polymers. This is probably due to the fact that gel permeation chromatography is not an absolute method for determining molecular weight, and does not take into account the microstructure of different polymers. A small decrease in polydispersity was also detected. This was attributed to the loss of lower molecular weight species during the purification procedure.

Molecular weights as high as 106 have been achieved for the phosphinimine-modified organic polymers. Also, some molecular weight control was possible using the anionic polymerization approach.

Conclusions

Cyclic phosphazene trimers can be linked to phosphinated organic polymers in near-quantitative yield. Because diphenyl-p-styrylphosphine can be polymerized both by free radical or anionic techniques, it is possible to form copolymers with a wide variety of organic monomers. Moreover, the use of phosphazene cyclic trimers with two or three azide groups is an efficient means to achieve polymer cross-linking under relatively mild conditions. The coupling reaction with phosphoryl azides provides an additional method for the incorporation of phosphorous into organic polymers.

EXAMPLE 2

Modification of Organic Copolymers with Diphenyl-p-Styrylphosphine and High Temperature Decomposition Pathways Monomer diphenyl-p-styrylphosphine (1) was polymerized anionically to yield poly(diphenyl-p-styrylphosphine). To better evaluate the phosphinimine approach utilized in Example 1 (anionic polymerization of monomer diphenyl-p-styrylphosphine (1) poly(diphenyl-p-styrylphosphine)) as a means to modify a variety of organic polymers, a series of copolymers of 1 with styrene or methyl methacrylate (MMA) were synthesized via free-radical addition techniques using AIBN as the initiator. In addition to molecular characterization by multinuclear NMR, gel permeation chromatography (GPC), and differential scanning calorimetry (DSC) techniques, the polymers were examined by thermogravimetric analysis (TGA) and oxygen index (OI) methods.

Experimental Procedure (1) Instruments $^{31}$P and $^1$H NMR spectra were recorded as described in Example 1. Molecular weights were estimated with a Hewlett-Packard HP1090 gel permeation chromatograph equipped with a HP-1037A refractive index detector and a Polymer Laboratories PL gel 10 μm column calibrated with polystyrene standards (Waters).

Samples were eluted with a 0.1 wt % solution of tetra-n-butylammonium nitrate in THF. Thermal weight loss measurements of the polyphosphazenes were made using a Perkin Elmer TGA-7 under an atmosphere of dry nitrogen at a flow rate of 30 cc/min. using a heating rate of 10° C./min. Glass transition temperatures were measured using a Perkin-Elmer DSC-7 system.

(2) Synthesis of Starting Materials

The diphenyl-p-styrylphosphine (Monomer 1 or Comonomer 1) was synthesized and polymerized as described in Example 1. Anionic and free radical polymerization and the reaction of both $N_3P_3(OC_6H_5)_5N_3$ and $—N_3P_3(OCH_2CF_3)_5N_3$ with poly(diphenyl-p-styrylphosphine) also were conducted as described in Example 1.

(3) Copolymerizations of Comonomer 1 with Styrene

Comonomer 1 was dissolved in freshly distilled toluene under an atmosphere of argon. Styrene was added to the reaction flask via syringe followed by addition of AIBN (0.0057 g/g total monomer feed). The reactions were then heated to 60° C. During the polymerization, the viscosity of the reaction mixtures noticeably increased. After 40 hr, the reactions were precipitated into MeOH. The resultant white polymers were then precipitated into hexanes (2×) to finish the purification. The copolymers were analyzed by multinuclear NMR, GPC, and DSC. The composition of the purified copolymers were very close to that of the initial monomer feed and were determined by comparing the $^1$H NMR integration of the aryl protons to that of the alkyl protons. Typical chemical shifts for both $^1$H and $^{31}$P NMR are demonstrated with polymer 2a. Monomer feed ratio (styrene:comonomer 1), $\%_{mol}$ incorporation of comonomer 1, and DSC results (when available) are given for each polymer in Table 2.

(i) Polymer 2a: $^{31}$P NMR (CD$_2$Cl$_2$) δ=−5.9 (s, 1P, (C$_6$H$_4$) P(C$_6$H$_5$)$_2$); $^1$H NMR (CD$_2$Cl$_2$) δ=7.6–6.2 (br m, ArH ), 2.3–0.9 (br m, CH and CH$_2$). Monomer feed ratio (styrene:monomer 1): 99:1; Mol % comonomer 1 incorporated: 1.

(ii) Polymer 2b: Monomer feed ratio (styrene: comonomer 1): 98:2, MOL % monomer 1 incorporated: 2.

(iii) Polymer 2c: Monomer feed ratio (styrene: comonomer 1): 95:5, MOL % monomer 1 incorporated: 5.

(iv) Polymer 2d: Monomer feed ratio (styrene: comonomer 1): 90:10, MOL % monomer 1 incorporated: 11.

(4) Phosphinimine Formation with Styrene Copolymer Systems

The copolymer was dissolved in freshly distilled toluene under an atmosphere of argon. The azido phosphazene trimer (2 eq/mol phosphine incorporated) was then added to the reaction flask. The reactions were heated to reflux, and their progress was monitored by $^{31}$P NMR. Reactions were generally complete within 72 hr. Purification of the reaction product began with first concentrating the reaction mixture via rotoevaporation followed by precipitation into MeOH. The polymers were then precipitated from THF into MeOH (1×) and hexanes (2×) followed by Soxhlet extraction with hexanes for 48 hr. The polymers were characterized by multinuclear NMR, GPC, and DSC.

(i) Polymer 3a: $^{31}$P NMR ($CD_2Cl_2$) δ=10.4 (d, 1P, ($C_6H_4$)($C_6H_5)_2P$=N—), 8.4 (d, 2P, P($OC_6H_5)_2$), 10.2 (m, ring P bound to phosphinimine); $^1$H NMR ($CD_2Cl_2$) δ=7.7–6.2 (m, ArH), 2.6–0.9 (m, CH and $CH_2$).

(ii) Polymer 4a: $^{31}$P NMR ($CD_2Cl_2$) δ=17.7 (d, 2P, P($OCH_2CF_3)_2$), 13.7 (d, 1P, ($C_6H_4$)($C_6H_5)_2P$=N—), 10.2 (m, 1P, ring P bound to phosphinimine); $^1$H NMR ($CD_2Cl_2$) δ=7.9–6.5 (br m, ArH ), 4.6–3.8 (br m, $OCH_2CF_3$), 2.6–1.2 (br m, CH and $CH_2$).

(5) Copolymerizations of Comonomer 1 with Methyl Methacrylate

Polymers 5a–5d were all prepared in a similar manner. The following preparation of is typical. Methyl methacrylate, comonomer 1, and AIBN (g AIBN/g total monomer feed=0.0057) were added in a Schlenk flask under an atmosphere of argon. Dioxane was added, and the flask was placed into a 60° C. water bath and stirred for 2 hrs. The resultant copolymer was precipitated into methanol, redissolved in dioxane and precipitated in hexanes (2×). The polymers were characterized by multinuclear NMR spectroscopy, GPC, and DSC. The results are shown in Table 3. The actual compositions of the copolymers differed from that of the monomer feed and were determined by $^1$H NMR spectroscopy. The ratio of the integration of the protons from the aromatic rings to the α-$CH_3$ hydrogen atoms were used to determine the mol % of comonomer 1 in each copolymer. Typical chemical shifts for both $^1$H and $^{31}$P NMR are demonstrated using polymer 5a. Monomer feed ratios and mol % comonomer 1 incorporated into the copolymers are listed below.

(i) Polymer 5a. $^{31}$P NMR ($CD_2Cl_2$), δ(ppm): −5.90 (s, 1P). $^1$H NMR ($CD_2Cl_2$), δ(ppm): 6.7–7.3 (ArH), 2.0–3.6 ($OCH_3$), 1.1–2.0 (CH and $CH_2$), 0.3–1.1 (α-$CH_3$). Monomer feed ratio (MMA:monomer 1): 99:1; MOL % comonomer 1 incorporated: 2.

(ii) Polymer 5b. Monomer feed ratio (MMA:comonomer 1): 98:2; MOL % comonomer 1 incorporated: 5.

(iii) Polymer 5c. Monomer feed ratio (MMA:comonomer 1): 95:5; MOL % comonomer 1 incorporated: 12.

(iv) Polymer 5d. Monomer feed ratio (MMA:comonomer 1): 90:10; MOL % comonomer 1 incorporated: 20.

(6) Phosphinimine Formation with

Methyl Methacrylate-Based Copolymer Systems

Polymers 6a–d and 7a–d were all prepared in a similar manner. The following preparation is typical. Polymer 5d and the phosphazene azide compound (1.5 eq. with respect to mol % 1 incorporated) were heated to reflux in dioxane for 72 hrs. The resultant polymer was purified by precipitating in hexanes (2×) and dried under vacuum. Polymers were characterized by multinuclear NMR spectroscopy, GPC, and DSC. $^1$H and $^{31}$P NMR spectra were very similar for all methyl methacrylate-based copolymers modified with both phosphazene azides. Typical chemical shifts are demonstrated with polymers 6d and 7d. GPC and DSC data (when available) are given in Table 3.

(i) Polymer 6d: $^{31}$P NMR ($CD_2Cl_2$), δ(ppm): 10.2 (d, 1P, ($C_6H_4$)($C_6H_5)_2P$=N—), 8.4 (d, 2P, ($C_6H_5O)_2P$), 6.0 (m, 1P, ring P bound to phosphinimine). $^1$H NMR ($CD_2Cl_2$), δ(ppm): 6.7–7.5 (m, ArH), 2.0–3.6 ($OCH_3$), 1.1–2.0 (CH and $CH_2$), 0.3–1.1 (m, α-$CH_3$).

(ii) Polymer 7d: $^{31}$P NMR ($CD_2Cl_2$), δ(ppm): 17.6 (d, 2P, ($CF_3CH_2O)_2P$), 13.4 (d, br. 1P, ($C_6H_4$)($C_6H_5)_2P$=N—, 10.3 (m, 1P, ring P bound to phosphinimine). $^1$H NMR ($CD_2Cl_2$), δ(ppm): 7.1–7.5 (ArH), 3.7–4.7 (m, $CF_3CH_2O$), 2.0–3.6 ($OCH_3$), 1.1–2.0 (CH and $CH_2$), 0.3–1.1 (m, α-$CH_3$).

(7) Pyrolysis of Model Compounds

Compounds 10 and 11 were prepared as described in Allcock, et al., Inorg. Chem., 38:5535 (1999). These were heated in the thermogravimetric analyzer under conditions identical to the TGA studies (30 cc/min. N, flow; 10° C. min heating rate). The volatiles were collected from the furnace vent on Tenax adsorbent packed inside a Pyrex tube. Suction on the vent was maintained with a Q-Max sampling pump (Supelco). The tubes were subsequently flushed with ethyl acetate to remove the volatile compounds. The residue left in the sample pan as well as the extracts from the tubes were analyzed by $^{31}$P and $^1$H NMR spectroscopy.

(8) Preparation of Polymer/Cyclic Trimeric Phosphazene Blends

Compounds 8 and 9 were prepared as described in Allcock, Phosphorus-Nitrogen Compounds (Academic Press, Inc.: New York. 1972). Blends were prepared from mixtures of 3.33 g polymer (polystyrene or PMMA) and 1.67 g phosphazene (8 or 9) were dissolved in methyl ethyl ketone (MEK). The solutions had a total volume of 50 mL and were cast into molds measuring 22.5 cm×17.5 cm. Slow evaporation of the solvent was obtained by covering both the mold and a reservoir of pure MEK with a loose covering of foil. The resultant blends containing 33 wt % phosphazene cyclic trimer were dried under vacuum to remove any residual solvent.

(9) Combustion Analysis

Modified oxygen indices were obtained through the use of a procedure developed for powdered samples. Following the techniques described in Catala, et al., Proc. $18^{th}$ Int. Conf. Org. Coat. Sci. Tech., 87–99 (1992); Reghunadhan Nair, et al., Polym. Deg. Stab., 26:305–31 (1989), a glass cup containing 200 mg of polymer powder was suspended inside an oxygen index instrument. This instrument was constructed according to the specifications of standard ASTM-D-2863–91. An atmosphere of nitrogen and oxygen of controlled composition was maintained with a purge flow of 17 L/min. A typical sample was then exposed to a propane flame for 10 seconds to ignite the polymer. The oxygen index (OI) was the concentration of oxygen necessary to sustain the combustion of the ignited polymer for exactly 30 seconds. In addition, the chars from the combustion of the copolymers and blends were analyzed for elemental composition.

(i) Polymer 2d. Elemental analysis calculated for $C_{80}H_{83}P$ (%): C, 89.9; H, 7.3; P, 2.8. Found for char: C, 86.81; H, 7.03; P, 3.75.

(ii) Polymer 3d. Elemental analysis calculated for $C_{113}H_{105}F_{15}N_4O_5P_4$ (%): C, 78.8; H, 6.1; N, 3.2; P, 7.2. Found for char: C, 44.36; H, 3.66; N, 4.70; P, 18.42.

(iii) Polymer 4d. Elemental analysis calculated for $C_{93}H_{90}F_{15}N_4O_5P_4$ (%): C, 63.8; H, 5.2; F, 16.2; N, 3.2;

P, 7.0. Found for char: C, 49.44; H, 3.74; F, 7.88; N, 2.58; P, 13.52.

(iv) Polymer 5c. Elemental analysis calculated for $C_{57}H_{76}O_{15}P$ (%): C, 69.8; H, 7.2; P, 4.5. Found for char: C, 72.60; H, 6.43; P, 5.89.

(v) Polymer 6c. Elemental analysis calculated for $C_{87}H_{101}N_4O_{20}P_4$ (%): C, 38.62; H, 2.92; F. 30.57; N, 6.01; P, 13.29. Found for char: C, 41.07; H, 3.14; N, 1.61; P, 20.97.

(vi) Polymer 7c. Elemental analysis calculated for $C_{67}H_{86}F_{15}N_4O_{20}P_4$ (%): C, 38.62; H, 2.92: F, 30.57; N, 6.01; P, 13.29. Found for char: C, 49.81; H, 4.59; F, 8.46; N, 2.59; P, 12.41.

(vii) Polystyrene/8 blend. Elemental analysis calculated for $C_{108}H_{102}N_3O_6P_3$ (%): C, 82.3; H, 6.6; N, 2.0; P, 4.5. Found for char: C, 51.52; H, 4.85; N, 1.96: P, 14.93.

(viii) Polystyrene/9 blend. Elemental analysis calculated for $C_{84}H_{84}F_{18}N_3O_6P_3$ (%): C, 68.1; H, 5.7; F, 15.6; N, 1.9; P, 4.2. Found for char: C, 88.64; H, 7.45; F, 1.08; N, 0.25; P, 0.75.

(ix) PMMA/8 blend. Elemental analysis calculated for $C_{107}H_{143}N_3O_{35}P_3$ (%): C, 60.6: H, 6.8: N. 2.0; P, 4.4. Found for char: C, 57.75; H, 6.86; N, 2.04; P, 4.85.

(x) PMMA/9 blend. Elemental analysis calculated for $C_{86}H_{131}F_{18}N_3O_{36}P_3$ (%): C, 46.4; H, 5.9; F, 15.5; N, 1.9; P, 4.2. Found for char: C, 51.16; H, 6.69; F, 11.77; N, 1.29; P, 2.70.

Results and Discussion (1) Styrene Based Copolymer Systems

Figure 5:
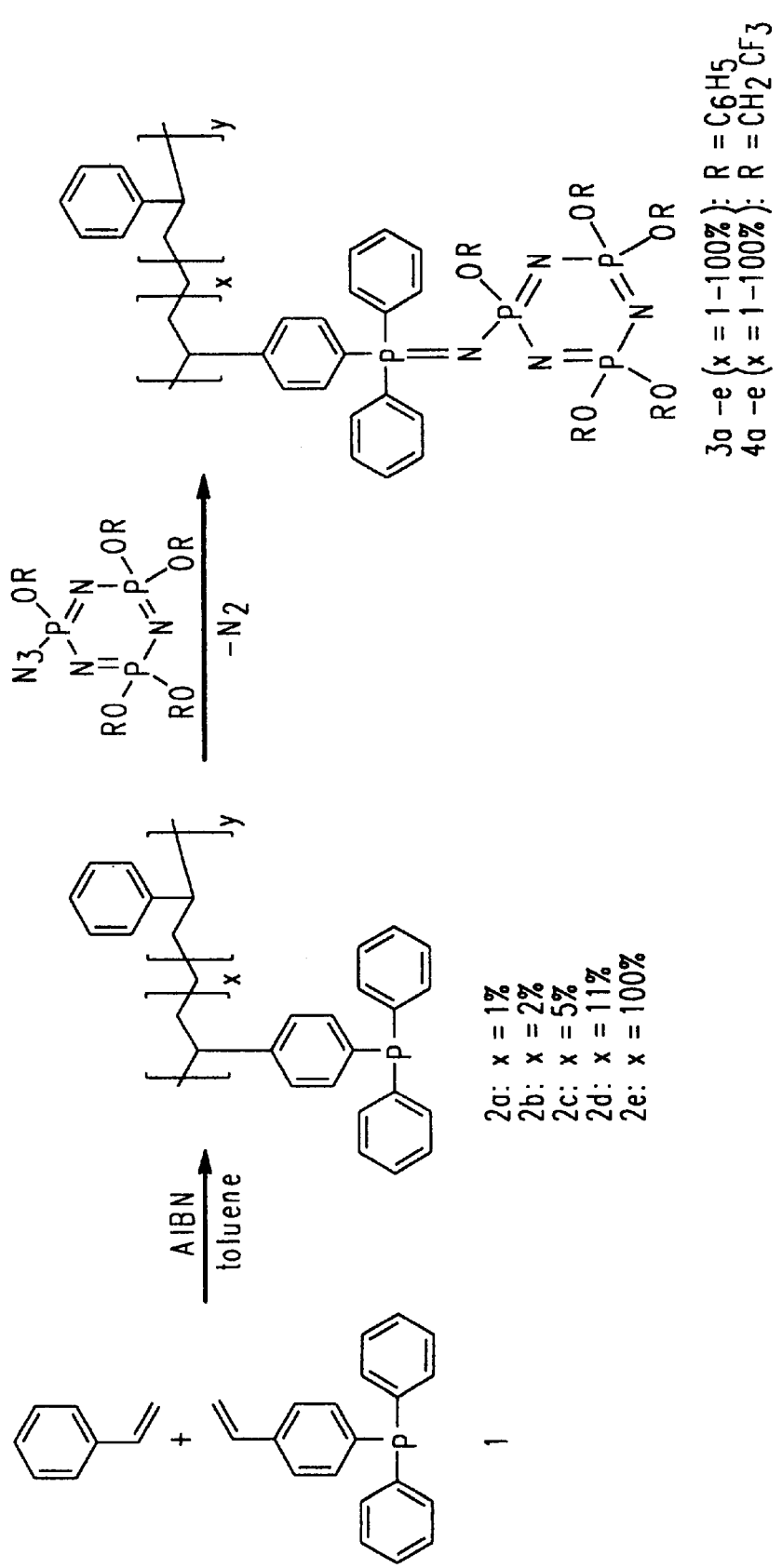
FIGS. 5 and 6 show copolymerization reaction schemes used in the Examples and the mole-percent of phosphine monomer incorporated into the organic polymers.
Figure 6:
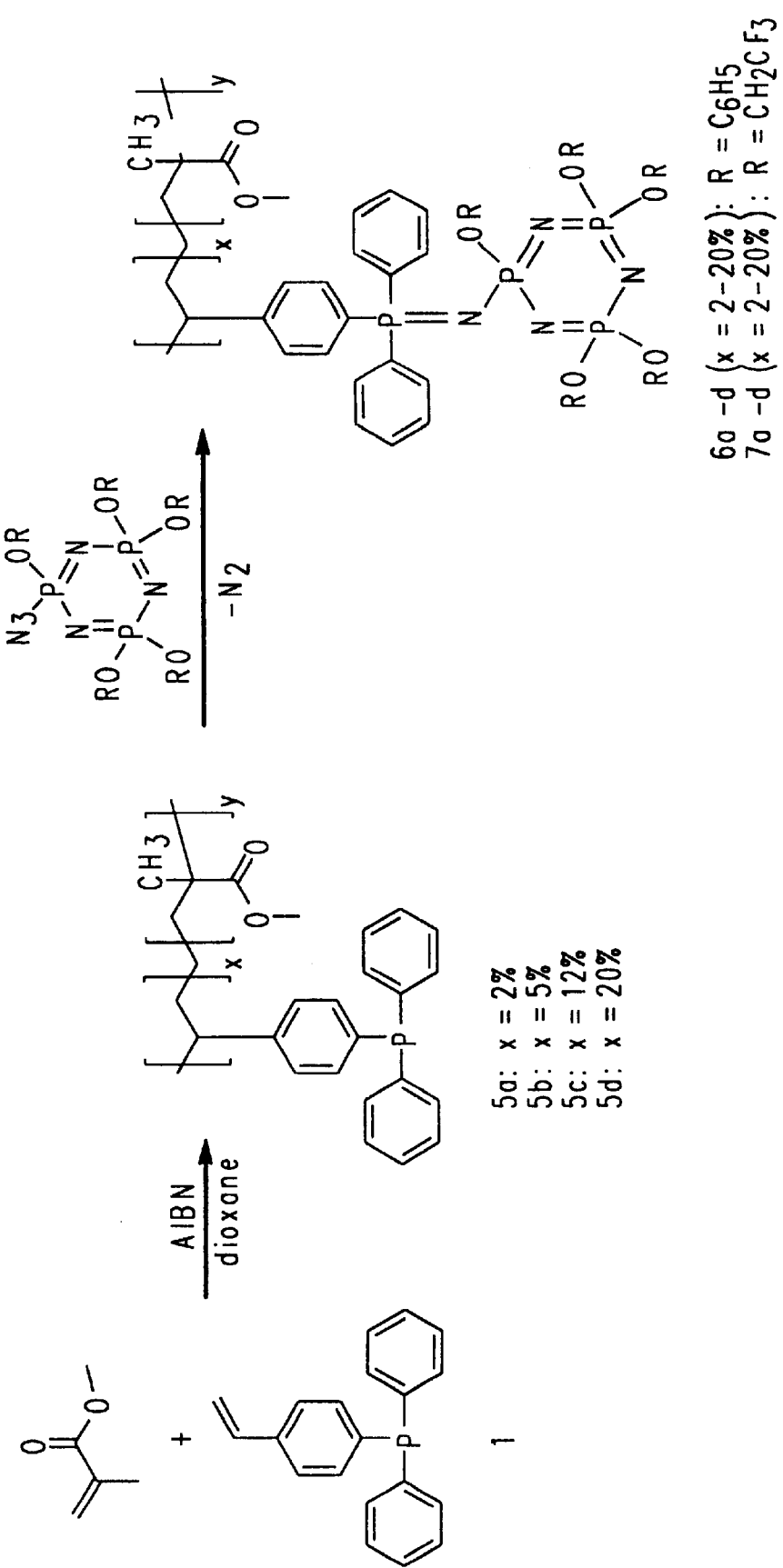

The copolymerization of monomer 1 with styrene was accomplished with toluene as a solvent at 60° C. over a period of 40 hr (FIG. 5). The monomer ratios in the styrene-based copolymers was very similar to that of the monomer feed ratios. The mol-percent phosphine monomer incorporated in the different copolymers are shown in FIGS. 5 and 6. Integration of the $^1$H NMR peaks was used to determine the mol-percent incorporation of monomer 1. The chemical shifts observed for the protons for each styrene copolymer were nearly identical. The copolymers were indistinguishable by $^{31}$P NMR.

(2) Methyl Methacrylate Based Copolymer Systems

The free radical copolymerization of monomer 1 with MMA was carried out with dioxane as the solvent at 60° C. for 2 hr. The $^1$H NMR resonance signals for polymers 5a–d were identical, except for a slight downfield shift of the aliphatic proton signals as the MMA percentage was increased. This shift is due to the shielding effect of the aromatic rings on the diphenyl-p-styrylphosphine units. This effect has also been noted for copolymers of MMA with styrene (San Roman, et al., Die Angewandte Makromolekulare Chemie, 78:129 (1979)). The copolymers were indistinguishable by $^{31}$P NMR spectroscopy. The final copolymers had a higher mol % incorporation of 1 than in the original monomer feed ratio as determined by $^1$H NMR. However, these values were reproducible for given a monomer feed ratio.

(3) Phosphinimine Modification

The various copolymers were then treated with the azidophosphazenes to generate the phosphinimine linkage. Reactions were carried out in refluxing toluene with an excess of the phosphazene azide. Complete conversion to the phosphinimine occurred under relatively mild conditions for each copolymer system. The progress of individual reactions was monitored by $^{31}$P NMR spectrometry. Diphenyl-p-styrylphosphine gives a singlet $^{31}$P peak at −6 ppm. Reaction with the cyclic phosphazene azido trimers causes this peak to disappear as a new peak, downfield from the first, appears as the phosphazene is converted to a phosphinimine unit. Each reaction was considered to be complete when the phosphine peak could no longer be detected. The exact location of the new phosphinimine peak depends on the cosubstituents linked to the cyclic phosphazene trimer. The reaction between $N_3P_3(OCH_2CF_3)_5(N_3)$ and Polymer 2e is a convenient example. Spectrum C is from the final product of this reaction as shown in FIG. 4. The phosphorus atom closest to the organic backbone, originally at −6 ppm (spectrum B), now appears at 13 ppm (spectrum C). The cyclophosphazene phosphorus atom originally bound to the azide unit shifts from near 17 ppm (spectrum A) to 11 ppm (spectrum C). The two phosphorus atoms furthest from the reaction center remain near 17 ppm (spectra A and C). A doublet is generated for these resonances due to splitting by the phosphorus atom originally bound to the azide. These chemical shifts are in good agreement with the results for small molecule analogues discussed in previous work (Allcock, et al., Inorg. Chem., 38:5535 (1999)). The integration of spectrum C is 1:1:2 for the peaks at 11 ppm, 13 ppm and 17 ppm, respectively, as expected for the repeat units containing four phosphorus atoms. The $^{31}$P NMR spectrum for each styrene based copolymer was very similar to the spectrum of the corresponding homopolymer. In some cases, a small percentage (<5%) of the phosphine was oxidized during the work up of the unmodified polymer. The oxidized phosphine has a $^{31}$P NMR chemical shift near 24 ppm. This peak remained unchanged after the polymer had reacted with the azide compounds.

(4) Gel Permeation Chromatography

Molecular weights for both the unmodified and modified copolymer systems were determined by gel permeation chromatography using polystyrene standards (Tables 2 and 3). The molecular weights of the modified copolymers were generally higher than those of their unmodified counterparts. In addition, the increases in molecular weight did not correspond to the theoretical values predicted by assuming complete conversion from the phosphine to the phosphinimine. For example, polymer 2e had an $M_n$ of 279,000. The introduction of the trifluoroethoxy substituted phosphazene cyclic trimer units would theoretically result in a polymer with $M_n$ of 903,000. The GPC suggested 4e to have an $M_n$ of 2,690,000, roughly three times larger than the calculated value. This could be due to the fact that gel permeation chromatography is influenced by the microstructures of the different polymer systems. The modified repeat units are much bulkier than those in the totally organic repeat units.

(5) Differential Scanning Calorimetry

DSC analysis provides an insight into the polymer microstructure, as well as the mechanical properties of the copolymer systems. A single glass transition temperature ($T_g$) was detected for each polymer examined, which suggests a random copolymer microstructure of the type normally obtained in free-radical polymerizations. A microstructure with blocks would generate two or three $T_g$'s.

The $T_g$'s of the styrene copolymers increased with increasing incorporation of diphenyl-p-styrylphosphine due to the bulk and rigidity of the phosphine-containing monomer. However the $T_g$'s of the cyclophosphazene-substituted copolymers were much lower than those of the corresponding unmodified copolymers. For example, styrene has a $T_g$ of 98° C. The $T_g$ of polymer 2d is 14° C. higher at 112° C. Incorporation of the cyclophosphazene lowered the $T_g$ to 83° C. for the fluorinated phosphinimine and 85° C. for the aryloxy phosphinimine. It seems possible that phosphazene cyclic trimers pendent to the polymer backbone increase the free volume of the system, thereby decreasing the $T_g$'s. The two different phosphazene trimers had very similar effects on $T_g$'s of the copolymers in spite of the extreme bulkiness of the aryloxy cyclophosphazene.

Increasing amounts of diphenyl-p-styrylphosphine in the MMA based copolymers decreased the $T_g$ slightly. This small effect reflects similarities between the $T_g$'s of the MMA and 1 homopolymers. The cyclophosphazene units had a much more pronounced effect on the mechanical properties. Only 10% of the phosphazene trimer decreased the $T_g$ of the unmodified copolymer by 30–40° C.

(6) Thermal Stability

The thermal stability of a polymer has significant, though not necessarily direct, influence on the fire resistance of that material. The thermal stabilities of the polymers were estimated by TGA using a nitrogen atmosphere and a heating rate of 10° C./minute. One of the main parameters reported is the temperature at which the polymer has lost 5% of its original weight, or $T_{5\%}$. The other parameter of interest is the weight of char remaining at a given temperature in terms of percent of the original weight. All char yields reported are essentially constant from the specified temperature up to 800° C. Although decomposition temperatures and char yields as determined by TGA cannot be used directly to predict flammability, they do give an indication of the tendency of a material to produce volatile compounds at high temperatures. In some cases, these volatiles can actually inhibit combustion by quenching the radical reactions within the flame, a process referred to as vapor phase flame retardance (Lewin in *Fire Retardancy of Polymers: The Use of Intumescence* (Le Bras, et al., eds.) (The Royal Society of Chemistry: Cambridge, UK. 1998)). However, for most organic polymers without flame retardant modification, volatile compounds from pyrolysis are generally flammable and act as fuel for the sustained burning of the polymer. Inhibition of the release of these volatiles, as indicated by an increase in $T_{5\%}$ or in the char yield, can often decrease the flammability of a material by reducing the supply of fuel to the flame (Cullis, et al., *Polymer*, 24:83–440 (1983)). Flame retardant action of this type said to occur by a condensed phase mechanism.

(a) Styrene Based Polymer Systems

Figure 7:
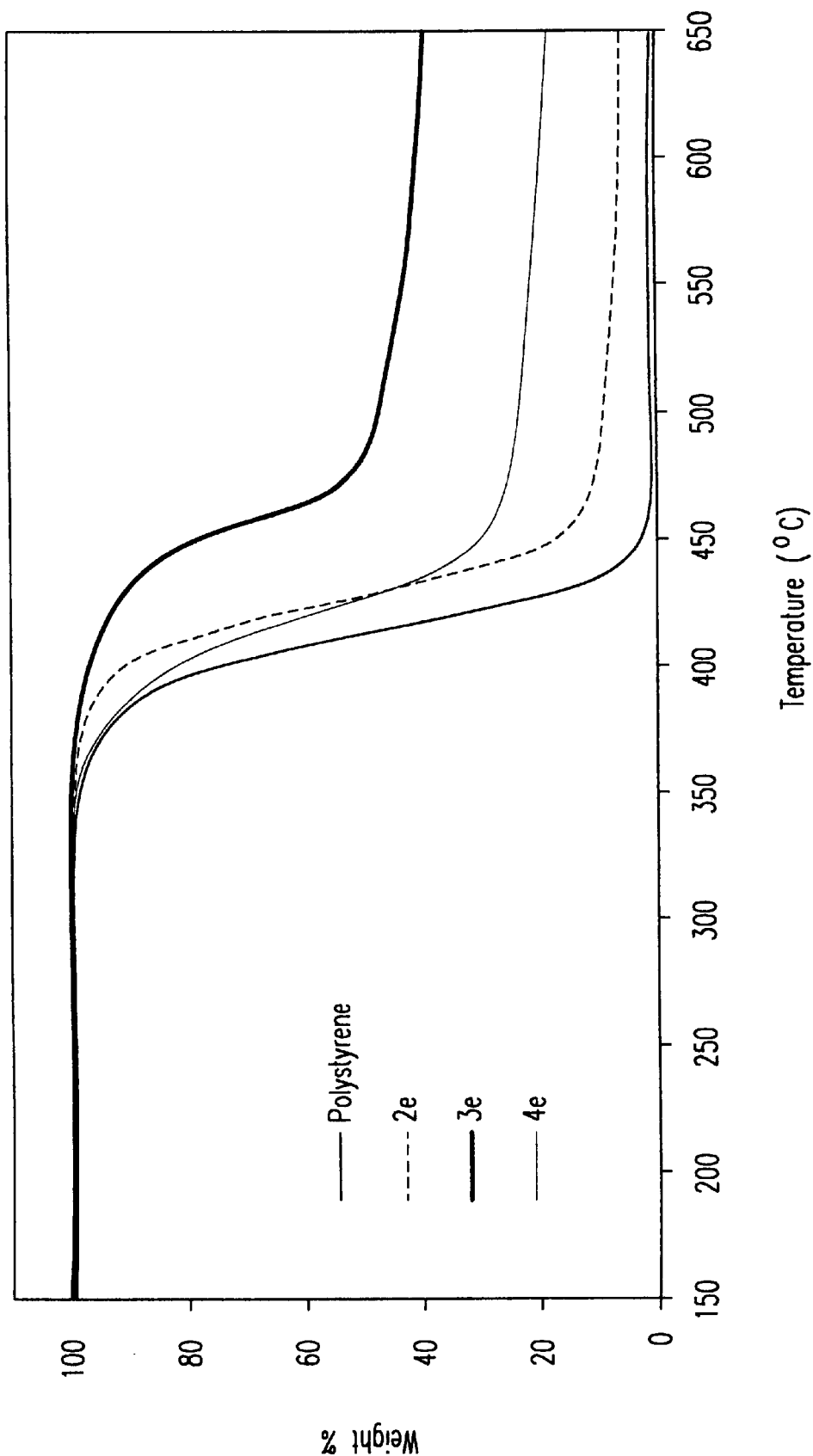
FIGS. 7–11 are graphs showing thermogravimetric analysis data (weight % polymer vs. temperature) for polystyrene and phosphazene-modified copolymer systems bases on polystyrene (FIGS. 7–9) and poly(methylmethacrylate) and phosphazene-modified copolymer systems bases on poly(methylmethacrylate) (FIGS. 10–11).

The weight loss curves for polystyrene, poly(diphenyl-p-styrylphosphine) (2e), and the phosphazene-modified homopolymers (3e, 4e) are shown in FIG. 7, and the weight loss data are given in Table 4. Pure polystyrene shows a $T_{5\%}$ at 374° C. A single-step decomposition follows, leaving less than 1% of the original material at 450° C. Polystyrene thermally depolymerizes by random chain scission into a mixture of styrene monomer, dimer, and trimer (McNeill, et al., *Polym. Deg. Stab.*, 28:131–51 (1990)). All of these products can act as fuel for combustion. Polymer 2e and its phosphazene modified derivatives 3e and 4e exhibit a similar one step weight loss. Polymer 2e has $T_{5\%}$ at a higher temperature relative to polystyrene (at 391° C.) and leaves a 5.9% char yield at 650° C. Thus, the main effect of the presence of phosphazene species is to increase the high temperature char yield. The trifluoroethoxy phosphazene derivative 4e has its $T_{5\%}$ at roughly the same temperature as that of unmodified polystyrene. However, the char yield is significantly increased to 18.2%. The aryloxy phosphazene derivative 3e has the best thermal behavior of all the polymers examined in this study. Its $T_{5\%}$ occurs almost 40° C. higher than that of polystyrene, and its char yield of 39.5% is roughly double that of 4e.

Figure 8:
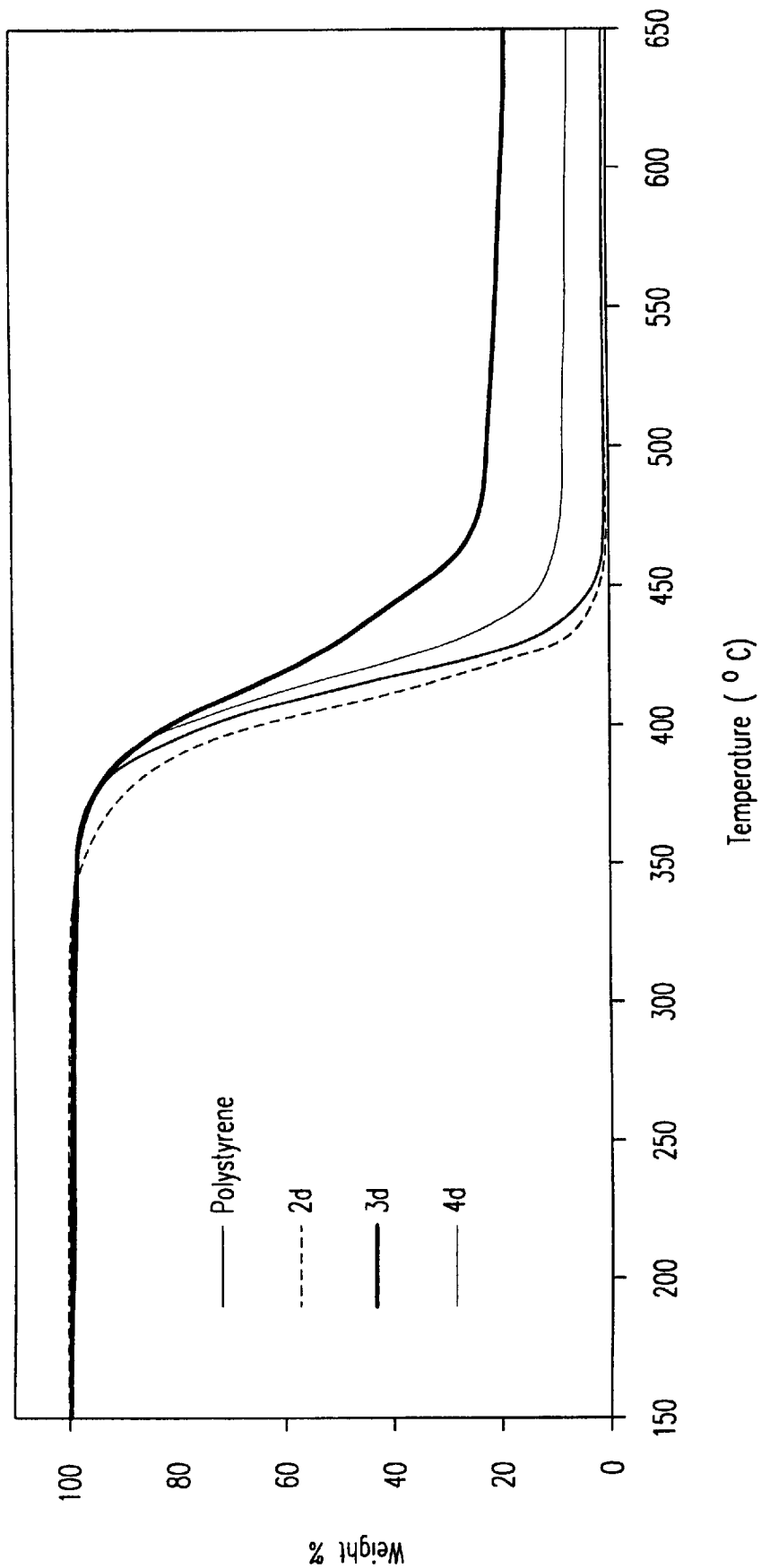
Figure 9:
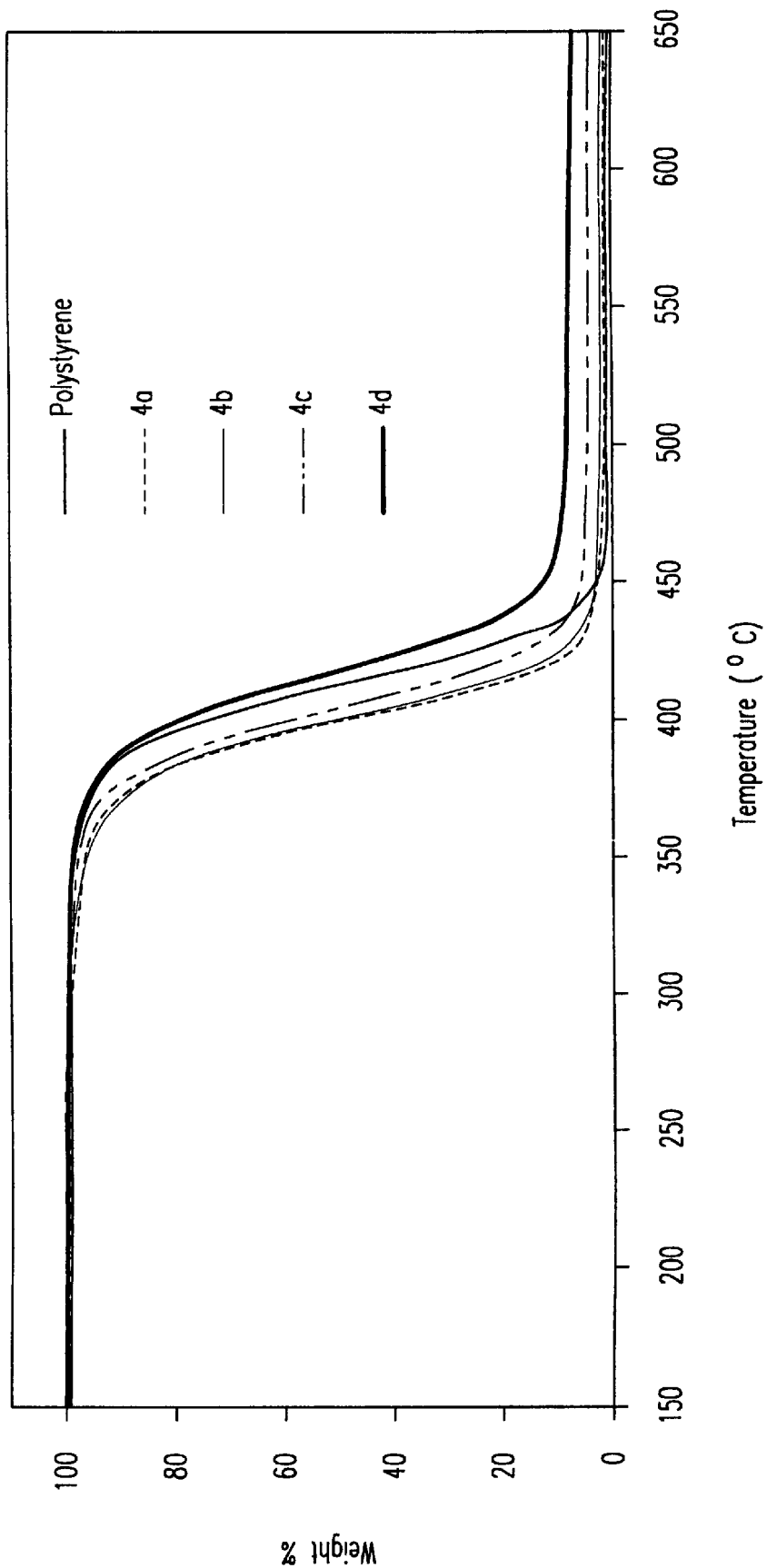

The TGA curves for the polystyrene copolymers with 10 mol % comonomer 1 incorporation are shown in FIG. 8, together with the weight loss curve of polystyrene for comparison. The curves for polystyrene and copolymers 4a–d shown in FIG. 9 illustrate the effect of the phosphazene loading on thermal degradation behavior. All the copolymers show the one-step weight loss that is characteristic of pure polystyrene. At this reduced loading, 2d actually shows a decrease in $T_{5\%}$ relative to that found for polystyrene as indicated in Table 5. The char yield for this copolymer is approximately the same as for polystyrene. The phosphazene derivatives 3 and 4 show no improvement in $T_{5\%}$ at the 10% loading and actually show a decrease in the initial thermal stability at lower incorporation levels. This effect is slightly more pronounced for the trifluoroethoxy derivatives. The $T_{5\%}$ falls to 360° C. for the 1 mol % copolymer 4a, which is slightly below that observed for 3a. Moreover, the incorporation of the trifluoroethoxy phosphazene appears to produce an upper limit for the initial thermal stability of the polymer. The $T_{5\%}$ rises with increasing amounts of the trifluoroethoxy phosphazene until the $T_{5\%}$ of unmodified polystyrene (374° C.) is reached in the case of the 10 mol % modified copolymer 4d. An increase in the trifluoroethoxy phosphazene loading up to 100 mol % does not result in an increase in $T_{5\%}$. However, for both types of phosphazenes, the char yield increases with increased concentration of phosphazene cyclic trimer in the copolymer. Again, the char from the aryloxy derivatives is roughly double those of the corresponding trifluoroethoxy derivatives.

The differences in the thermal degradation of the cyclophosphazene-modified copolymers are a result of the chemical identity of the side groups. Because the two phosphazene cyclic trimers themselves have approximately equal molar masses, copolymers 3a–e and 4a–e contain almost identical concentrations by weight of phosphazene for a given mol % loading. The behavior of the small molecules, hexa(phenoxy)cycylotriphosphazene (8) and hexa(trifluoroethoxy)cyclotriphosphazene (9), at elevated temperatures has been well documented (Maynard, et al., *Macromolecules*, 24:2794–99 (1991); Allcock, et al., *Chem. Mater.*, 2:425–32 (1990); Peddada, et al., *Macromolecules*, 16:1258–64 (1983)). In an inert atmosphere, 9 volatilizes at 300° C. without significant decomposition. However, compound 8 does not begin to volatilize until 400° C. under identical conditions, and this process competes with a crosslinking reaction between cyclic trimers. In the polymers examined here, this crosslinking reaction probably occurs during the main weight loss step as detected by TGA. Compound 9 has both a higher volatility and a reduced tendency to undergo crosslinking reactions than 8. Thus, smaller amounts of char are generated from the trifluoroethoxy derivatives. It is also possible that the phosphazenes inhibit radical depolymerization reactions by physically diluting the polymer matrix.

(b) Methyl Methacrylate Based Polymer Systems

Figure 10:
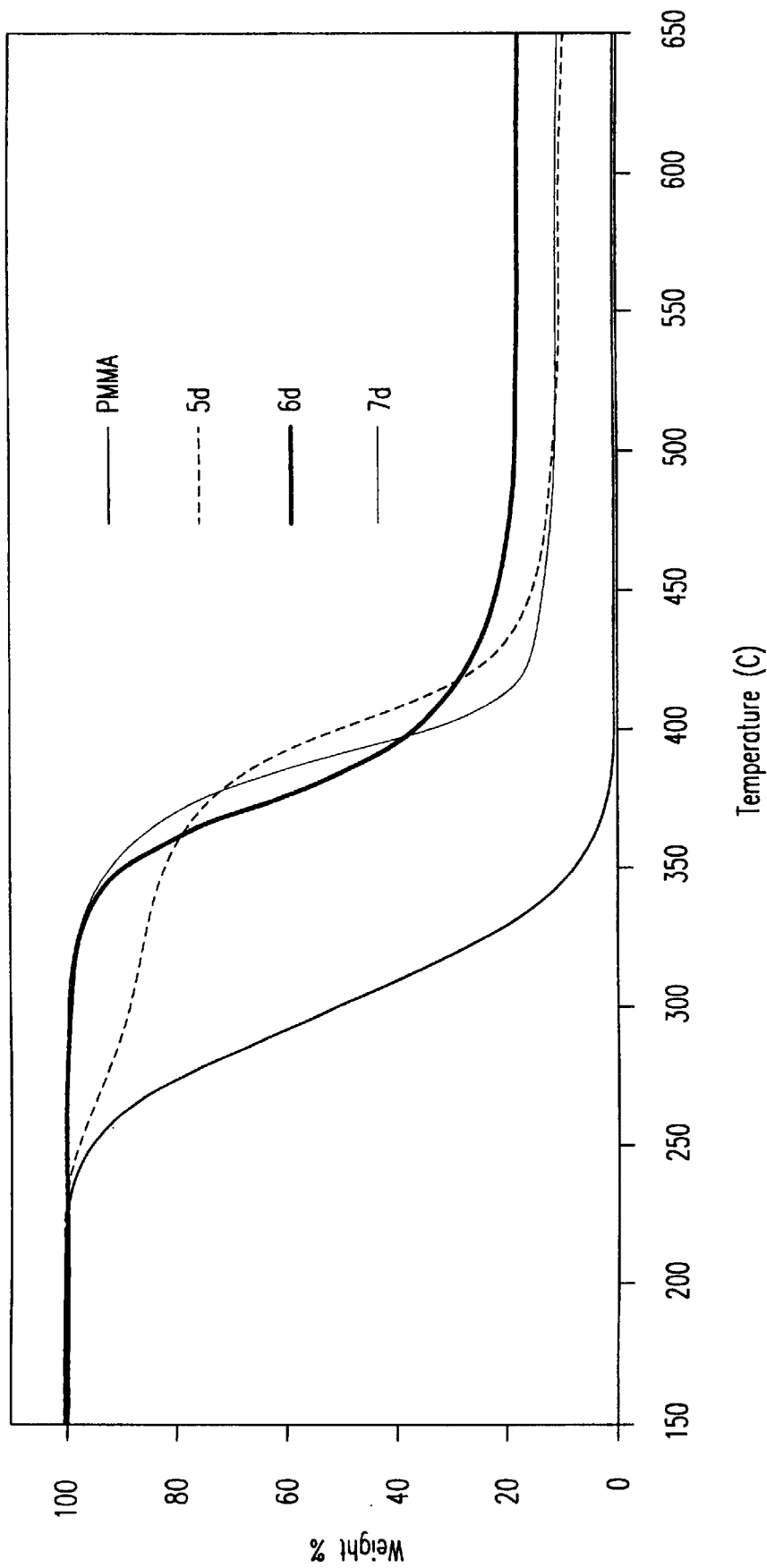
Figure 11:
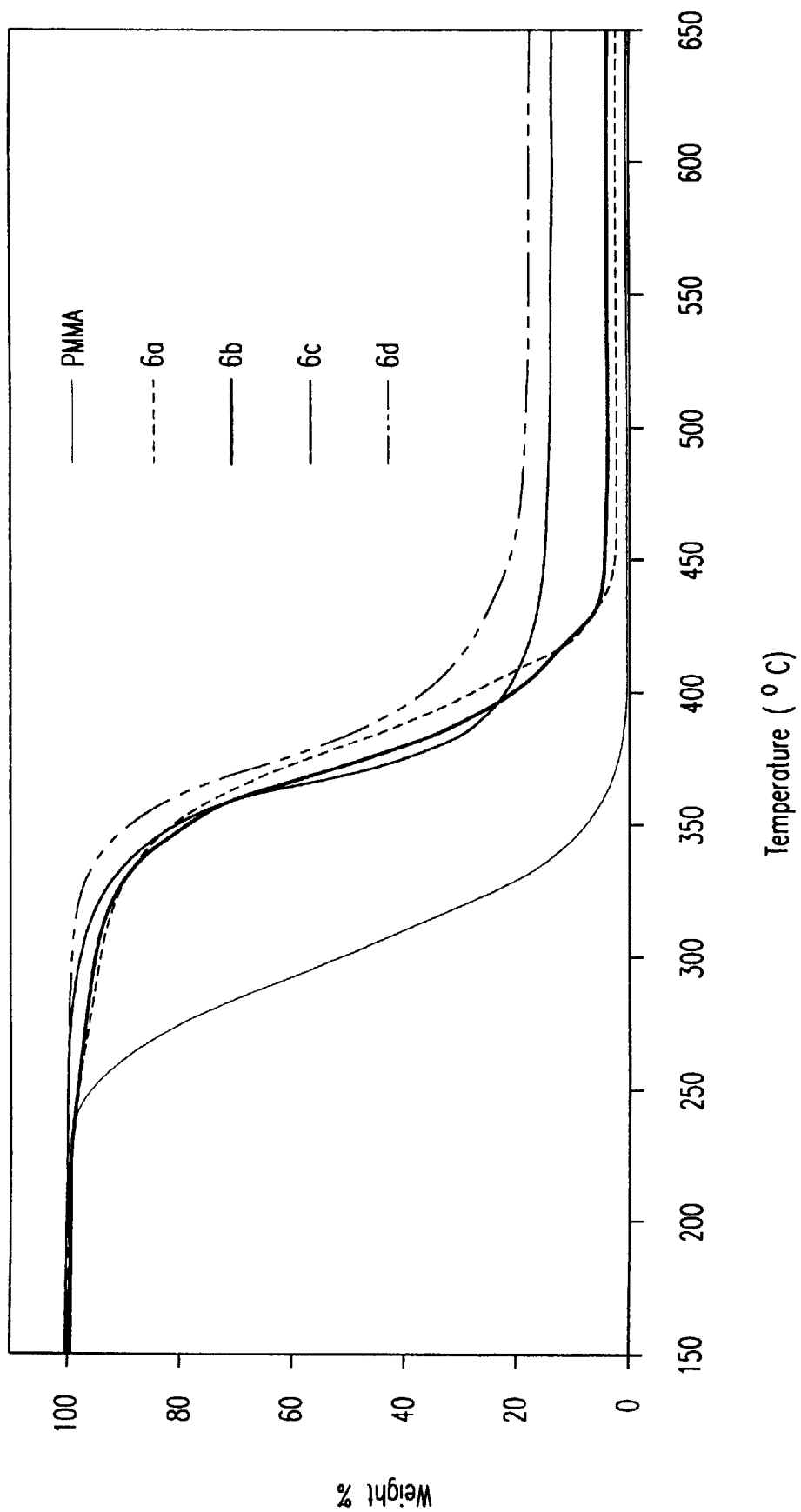

The TGA curves for the poly(methyl methacrylate) copolymers with 20 mol % comonomer 1 incorporation are shown in FIG. 10, and data for copolymers 5a–d, 6a–d, and 7a–d are given in Table 7. Pure PMMA has its $T_{5\%}$ at 252° C., more than 100° C. below that of polystyrene. Minimal char is left by 400° C. as PMMA depolymerizes almost completely to monomer (McNeill, et al., *Eur. Polym. J.* 4:21–30 (1968)). The copolymer of MMA with 20 mol % comonomer 1 (5d) shows a two step weight loss. The first step begins at a temperature close to that for PMMA, but only 15% of the original weight is lost in this step. The second step occurs closer to the $T_{5\%}$ of poly(diphenyl-p-styrylphosphine). This second step leaves slightly less than 20% of the original weight at 650° C. Dramatic increases in $T_{5\%}$ occur following incorporation of the phosphazenes into the polymer side groups. The two-step weight loss found for 5d is not observed with the 20% phosphazene derivatives. However, the lower loadings of cyclic phosphazenes do show a slight weight loss before the main decomposition step as can be seen for copolymers 6a–d in FIG. 11. The char yields for the phosphazene-functionalized copolymers are reduced by roughly 30% relative to their polystyrene copolymer counterparts. This is in sharp contrast to the increase in char yield for 5d as compared to the copolymer of styrene with 10 mol % comonomer 1 (2d).

Poly(methyl methacrylate) produced by free radical addition has been shown to degrade by a two-step mechanism (McNeill, et al., *Eur. Polym. J.*, 4:21–30 (1968)). The first step involves depolymerization from the chain ends and occurs between 220° C. and 300° C. This is followed by random chain cleavage at temperatures between 320° C. and 350° C. This polymer can be stabilized to higher temperatures simply by the incorporation of an organic comonomer such as styrene or various alkyl acrylates. The presence of the comonomer inhibits the depolymerization of PMMA by blocking the unzipping process that generally begins at the chain ends (McNeill, et al., *Eur. Polym. J.*, 4:21–30 (1968)). The thermal degradation behavior detected for 5d is consistent with this mechanism. Some initial depolymerization from chain ends still occurs for this copolymer, as indicated by the initial loss in weight at 250° C.; but the phosphine units interfere the progress of this degradation. The strong char-forming effect of the phosphine is probably due to a reaction of the phosphorus (III) species with the carbonyl groups of the MMA to produce phosphorus esters (Brown, et al., *J. Polym. Sci., A.*, 24: 1297–311 (1986)). Copolymer 5d is more efficient in forming high temperature char than either of the cyclophosphazene-containing copolymers because its weight percent of comonomer 1 is only half that of the phosphazene derivatives. Copolymer 6d and 7d contain no phosphorus (III), and char formation is probably due to the same mechanism that operates in the polystyrene copolymers. This mechanism is sensitive to the polymer matrix as is evidenced by the reduction in char yield for the PMMA copolymers. However, the presence of the phosphazene does serve to inhibit the initial depolymerization of PMMA from the chain ends.

(c) Model Compound Studies

To further understand the thermal degradation of these copolymers, pyrolysis studies of model compounds 10 and 11 were undertaken. Heating compound 10 to 400° C. gave an insoluble, glassy char. Heating to temperatures of 200° C. and 300° C. resulted in the formation of the same char beneath a layer of clear oil. This oil had the same characteristics as 10, as did the volatiles collected from the pyrolysis. Compound 11 gave no char or volatiles below 400° C. Analysis by $^{31}$P and $^1$H NMR spectroscopy indicated no change from the original spectra.

The ability of 10 to volatilize without fragmentation or rearrangement indicates that it can act as a vapor phase flame retardant, as has been observed for 9 (Allen, *J. Fire Sci.*, 11:320–28 (1993)). Once depolymerization of the polymer backbone has occurred, the comonomer 1 is liberated and can undergo simultaneous crosslinking and volatilization. Hexaphenoxy cyclotriphosphazene is known to undergo crosslinking reactions only above 400° C. As seen here, no observable rearrangement or volatilization occurs below this temperature. Even after depolymerization of the backbone, the aromatic phosphazene comonomer will not vaporize into a flame front but will enhance char formation through crosslinking reactions.

(7) Fire Resistance

The flammabilities of the copolymers of styrene with 10 mol % comonomer 1 (2d) and its cyclophosphazene-modified derivatives (3d and 4d) as well as the copolymers of MMA with 10 mol % comonomer 1 (5c) and its cyclophosphazene-modified derivatives (6c and 7c) were examined by a modification of oxygen index (OI) analysis. These results were compared to the flammabilities of pure polystyrene and PMMA. The OI is defined as the concentration of oxygen necessary to sustain the flaming combustion of a material in a controlled nitrogen and oxygen atmosphere. Materials with high OI values are considered to be more flame resistant since more oxidant is necessary to sustain a burning flame. The modified method employed here has been shown to yield reproducible results which are useful for comparing the effects of flame retardant treatments within a specific polymer system (Catala, et al., *Proc. 18$^{th}$ Int. Conf: Org. Coat. Sci. Tech.*, 87–99 (1992); Reghunadhan Nair, et al., *Polym. Deg. Stab.*, 26:305–31 (1989)). The copolymers containing approximately 10 mol % comonomer 1 (2–4d, 5–7c) should give the most practical indication of the effectiveness of phosphazene modification for improving the fire resistance of these polymers.

(a) Styrene Based Polymer Systems

As measured by this method, polystyrene has an OI of 22. Incorporation of 10 mol % phosphine does not increase the flame resistance of the polymer at all. It does, however, yield a small amount of solid char after combustion, in contrast to polystyrene which leaves no residue. Significant increases in flame resistance are observed following incorporation of phosphazene rings into the side groups. The halogenated derivative 4d has an OI of 28, and the aromatic derivative 3d has an OI of 33. For these polystyrene copolymers, flame resistance correlates with char formation at high temperatures as measured by TGA. The elemental compositions of the chars from combustion are shown in Table 6 in terms of molar ratios of phosphorus to carbon, phosphorus to nitrogen, and phosphorus to fluorine. The ratio of phosphorus to carbon (P/C) increases by 50% after the combustion of 2d. The char formation for 2d most likely involves the conversion of the phosphorus (III) species into a phosphoryl derivative. The char from this copolymer contains an equimolar ratio of phosphorus and oxygen, suggests an oxidation of the phosphine. The phosphazene containing copolymers show more dramatic increases in P/C in the range of 400% for 3d and 170% for 4d. Because the phosphorus atoms are preferentially incorporated into the char, a condensed phase mechanism is probably responsible for part of the fire retardance in all of these copolymers. This is much more obvious for the phosphazene-modified copolymers, especially the aryloxy derivative. Both of the phosphazene-containing copolymers show increases in the ratio of phosphorus to nitrogen (P/N) in the char relative to the original material. Also, 4d shows a 300% increase in the ratio of phosphorus to fluorine (P/F) following combustion, which indicates that side groups are eliminated during this process. These increases in P/N and P/F show that significant rearrangements of the phosphazenes occur under oxidizing conditions at high temperatures. This is in contrast to the pyrolysis behavior which showed no rearrangement in an inert atmosphere. Both nitrogen-containing compounds and halogenated compounds can act as vapor phase flame retardants, thus enhancing the total flame retardant effect of the phosphazene species (Lewin in *Fire Retardancy of Polymers: The Use of Intumescence* (Le Bras. et al., eds.) (The Royal Society of Chemistry: Cambridge, UK, 1998)). However, the vapor phase effect of the fluorine in 4d does not compensate for the lack of a condensed phase flame retardance.

Flammability studies were also conducted on physical blends of polystyrene with 33 wt % of small molecules 8 or 9. These blends had approximately the same loading by weight of phosphazene as the corresponding 10 mol % phosphorus-bearing copolymers. The blend with 8 was optically clear, indicating good miscibility of the additive with the polymer. Analysis by DSC showed a $T_g$ of 50° C. A lack of compatibility between polystyrene and 9 was indicated by a visible phase separation after casting. For this blend, a $T_g$ at 97° C. was detected, as was a melting transition at 50° C. for 9. The flammabilities of these blends were greatly reduced relative to the analogous copolymers 3d and 4d. The OI of the blend with small molecule 8 was 45, and that of the blend with 9 was 35. Apparently, the flame retardant effects of the phosphazenes are increased if the additive is not bound to the polymer matrix. In the case of the blend with 9, elemental analysis of the char showed an 88% decrease in P/C, indicating the loss of most of the phosphazene. Fire retardance in this case seems to be due almost exclusively to a vapor phase mechanism. On the other hand, the blend with 8 showed roughly the same amount of increase in P/C compared to 3d but almost twice as much of an increase in P/N. The loss of nitrogen relative to phosphorus suggests that nitrogen-containing compounds inhibit combustion in the vapor phase for the blend with 8, complementing the condensed phase action typical of aryloxy phosphazenes.

(b) Methyl Methacrylate Based Polymer Systems

Poly(methyl methacrylate) had an OI of 17 in our studies, which indicates a high level of combustibility. In this case, incorporation of 10 mol % diphenyl-p-styrylphosphine slightly improved the flame resistance as reflected in an increase in the OI to 20. The addition of phosphazene rings improved the flame resistance further, but without any correlation with char formation. In fact, the aromatic derivative 6c increases the OI to only 22 even though it yields the highest char (TGA) of the copolymers of MMA with 10 mol % comonomer 1 and its phosphazene-modified derivatives. The fluorinated derivative 7c had an OI of 27, similar to that of the polystyrene copolymer. A vapor phase mechanism thus seems to be dominant for this system (Green, *J. Fire Sci.*, 14:426–42 (1996)). The trifluoroethoxy phosphazene is expected to be more effective in quenching the radicals present in the flame, due to both its increased volatility relative to the phenoxy phosphazene and the presence of large amounts of halogen in the side groups. This is supported by the elemental analysis of the chars from combustion. The increase in the P/C ratio for the char of 5c is 110%, approximately double that of the char from 2d, and an increase in the phosphorus to oxygen ratio of 230% is observed. Although this indicates a substantial increase in the amount of condensed phase flame retardant activity, only minimal improvement in the overall fire resistance was detected. Likewise, the char from 6c showed an increase in P/C that is equal to that of 3d, but a comparable flame retardant effect was not observed. The char from 7c showed an increase in P/C of only 88%, roughly half of the increase seen for its polystyrene copolymer counterpart (4d). Thus, for the trifluoroethoxy system, more phosphazene is released into the flame front from the PMMA copolymer than from the polystyrene copolymer. The increase in vapor phase flame retardance compensates for the reduced char formation.

Unlike the polystyrene system, the blending of PMMA with 8 and 9 did not dramatically increase the fire resistance. Both phosphazene cyclic trimers were compatible with PMMA as evidenced by the formation of clear films and by presence of single $T_g$'s at 60° C. for the blend with 8 and 55° C. for the blend with 9. The OI for both blends was 24. The presence of phosphazene cyclic trimers as additives instead of as covalently bound comonomers has a negligible impact on the degradation mechanism of PMMA. Neither $T_{5\%}$ nor the char yield of PMMA are altered by the presence of the additives. Without a comonomer present to inhibit the chain scission reactions, the majority of the flame retardant activity must occur through the action of the phosphazene cyclic trimer in the vapor phase. Because both 8 and 9 volatilize above the depolymerization temperature of PMMA, there is much less likelihood of an interaction between the phosphazene flame retardant and the combustion of MMA monomer. Elemental analysis of the chars for these blends gives no evidence for rearrangement in that the P/N and P/F ratios are not changed significantly. The difference in volatility of the phosphazenes is again observed as the blend with 8 shows a slight increase in P/C, and the blend with 9 shows a decrease.

Conclusions

The incorporation of cyclophosphazene trimers into organic copolymers via phosphinimine formation is an effective method to modify a wide variety of organic polymers. This technique allows for control of the structure and properties of the copolymers by variation of both the ratio of functionalized comonomers to non-functionalized comonomers and also the nature of the cosubstituents on the cyclic phosphazene azide. Because this method relies on the controlled modification of preformed organic polymers, the effects of phosphazene structure on the properties of the copolymers can be analyzed in a more straightforward manner than has been previously possible.

Pendent phosphazene cyclic trimers inhibit the thermal degradation of polystyrene by increasing the char yield at high temperatures through crosslinking reactions. Their effect on the decomposition of PMMA becomes manifest as an increase in the temperature at which volatile compounds are released. The fire resistance of polystyrene is improved due to a condensed phase mechanism, and the aryloxy phosphazene is more effective than the trifluoroethoxy phosphazene in this system. This pattern is reversed for PMMA, where vapor phase flame retardant effects are dominant. The fluorinated cyclic phosphazene covalently bound to the polymer is the most effective in this case.

TABLE 2

GPC Data for Styrene-based Copolymer Systems

| Polymer | Mol % 1 | $M_n$ | PDI |
|---|---|---|---|
| Polystyrene | 0 | 19,000 | 1.7 |
| 2a | 1.0 | 47,000 | 1.8 |
| 2b | 1.7 | 44,000 | 1.6 |
| 2c | 4.8 | 43,000 | 1.4 |
| 2d | 11.2 | 39,000 | 1.7 |
| 2e[a] | 100 | 279,000 | 1.7 |
| 3a | 1 | 52,000 | 1.6 |
| 3b | 1.7 | 45,000 | 1.6 |
| 3c | 4.8 | 49,000 | 1.4 |

TABLE 2-continued

GPC Data for Styrene-based Copolymer Systems

| Polymer | Mol % 1 | $M_n$ | PDI |
|---|---|---|---|
| 3d | 11.2 | 48,000 | 1.6 |
| 3e | 100 | 965,000 | 1.6 |
| 4a | 1.0 | 47,000 | 1.6 |
| 4b | 1.7 | 47,000 | 1.6 |
| 4c | 4.8 | 49,000 | 1.4 |
| 4d | 11.2 | 54,000 | 1.4 |
| 4e | 100 | 2,690,000 | 1.5 |

[a]anionic polymerization

TABLE 3

GPC Data for MMA Copolymer Systems

| Polymer | Mol % 1 | $M_n$ | PDI |
|---|---|---|---|
| PMMA | 0 | 140,000 | 1.9 |
| 5a | 2 | 133,000 | 2.0 |
| 5b | 5 | 140,000 | 1.9 |
| 5c | 12 | 146,000 | 1.8 |
| 5d | 20 | 142,000 | 1.8 |

TABLE 3-continued

GPC Data for MMA Copolymer Systems

| Polymer | Mol % 1 | $M_n$ | PDI |
|---|---|---|---|
| 6a | 2 | 137,000 | 2.0 |
| 6b | 5 | 140,000 | 1.9 |
| 6c | 12 | 195,000 | 1.7 |
| 6d | 20 | 339,000 | 1.8 |
| 7a | 2 | 136,000 | 2.3 |
| 7b | 5 | 130,000 | 2.2 |
| 7c | 12 | 238,000 | 1.6 |
| 7d | 20 | 219,000 | 1.8 |

TABLE 4

Thermal Properties of Polystyrene and Derivatives

| Polymer | $T_g$ (° C.) | $T_{5\%}$ (° C.) | Char at 650 (wt %) |
|---|---|---|---|
| Polystrene | 98 | 374 | 0.7 |
| 2e | 117 | 391 | 5.9 |
| 3e | 69 | 412 | 39.5 |
| 4e | 54 | 373 | 18.2 |

TABLE 5

Thermal Properties and Flammability of Copolymers Containing 10 mol % Comonomer

| Polymer | $T_g$ (° C.) | $T_{5\%}$ (° C.) | Char at 650 (wt %) | OI |
|---|---|---|---|---|
| Polystyrene | 98 | 374 | 0.7 | 22 |
| 2d | 112 | 364 | 0.8 | 22 |
| 3d | 85 | 376 | 18.7 | 33 |
| 4d | 83 | 377 | 7.1 | 28 |
| PMMA | 127 | 252 | 0.5 | 17 |
| 5c | 123 | 264 | 9.6 | 20 |
| 6c | 83 | 337 | 17.6 | 22 |
| 7c | 90 | 341 | 10.5 | 27 |

TABLE 6

Elemental Composition of Chars from Combustion of Polystyrene Copolymers and Blends

| Molar ratio | 2d calc. | 2d char | 3d calc. | 3d char | 4d calc. | 4d Char | 8 blend calc. | 8 blend char | 9 blend calc. | 9 blend char |
|---|---|---|---|---|---|---|---|---|---|---|
| P/C | 0.011 | 0.017 | 0.032 | 0.161 | 0.039 | 0.106 | 0.021 | 0.112 | 0.024 | 0.003 |
| P/N | — | — | 1.00 | 1.77 | 1.00 | 2.37 | 1.00 | 3.40 | 1.00 | 1.40 |
| P/F | — | — | — | — | 0.266 | 1.10 | — | — | 0.167 | 0.333 |

TABLE 7

Elemental Composition of Chars from Combustion of Poly(methyl methacrylate) Copolymers and Blends

| Molar ratio | 5c calc. | 5c char | 6c calc. | 6c char | 7c calc. | 7c Char | 8 blend calc. | 8 blend char | 9 blend calc. | 9 blend char |
|---|---|---|---|---|---|---|---|---|---|---|
| P/C | 0.015 | 0.031 | 0.042 | 0.200 | 0.053 | 0.100 | 0.028 | 0.033 | 0.035 | 0.020 |
| P/N | — | — | 1.00 | 5.90 | 1.00 | 2.20 | 1.00 | 1.08 | 1.00 | 0.95 |
| P/F | — | — | — | — | 0.269 | 0.909 | — | — | 0.167 | 0.141 |

EXAMPLE 3

Synthesis of Phosphazene-Modified Polysiloxanes

Overview

Polysiloxanes were modified by the incorporation of various cyclic phosphazenes, attached as pendent groups, onto the siloxane backbone. Hydrosilylation chemistry was used to covalently link diphenyl-p-styrylphosphine, monomer 1, to the backbone of various poly(dimethylsiloxane)-co-poly(hydromethylsiloxane)s (PDMS-co-PHMS). Mono azide cyclic phosphazene, such as $N_3P_3(OCH_2CF_3)_5N_3$, were then allowed to undergo a nitrene insertion reaction with the diphenyl-p-styrylphosphine to produce polysiloxanes with pendent phosphazene units. The polymers were characterized by multinuclear NMR, gel permeation chromatography (GPC), and differential scanning calorimetry (DSC).

Experimental Procedure (1) Instruments $^{31}$P and $^1$H spectra were recorded as described in Examples 1 and 2. Infrared spectra were recorded on a Perkin Elmer 1600 Series FTIR using BaF$_2$ salt crystals (25 mm dia., 4 mm thick).

(2) Procedure

Diphenyl-p-styrylphosphine (monomer 1) was synthesized as described above, and the synthesis of N$_3$P$_3$R$_5$N$_3$ was conducted as described in Allcock, et al., *Inorg. Chem.*, 38:5535 (1999). PDMS-co-PHMS, [Me$_2$Si-O]$_x$—[HMeSi-O]$_y$, was purchased from Gelest. 1,3-divinyltetramethyldisiloxane-platinum complex was purchased from Aldrich or Gelest.

Figure 12:
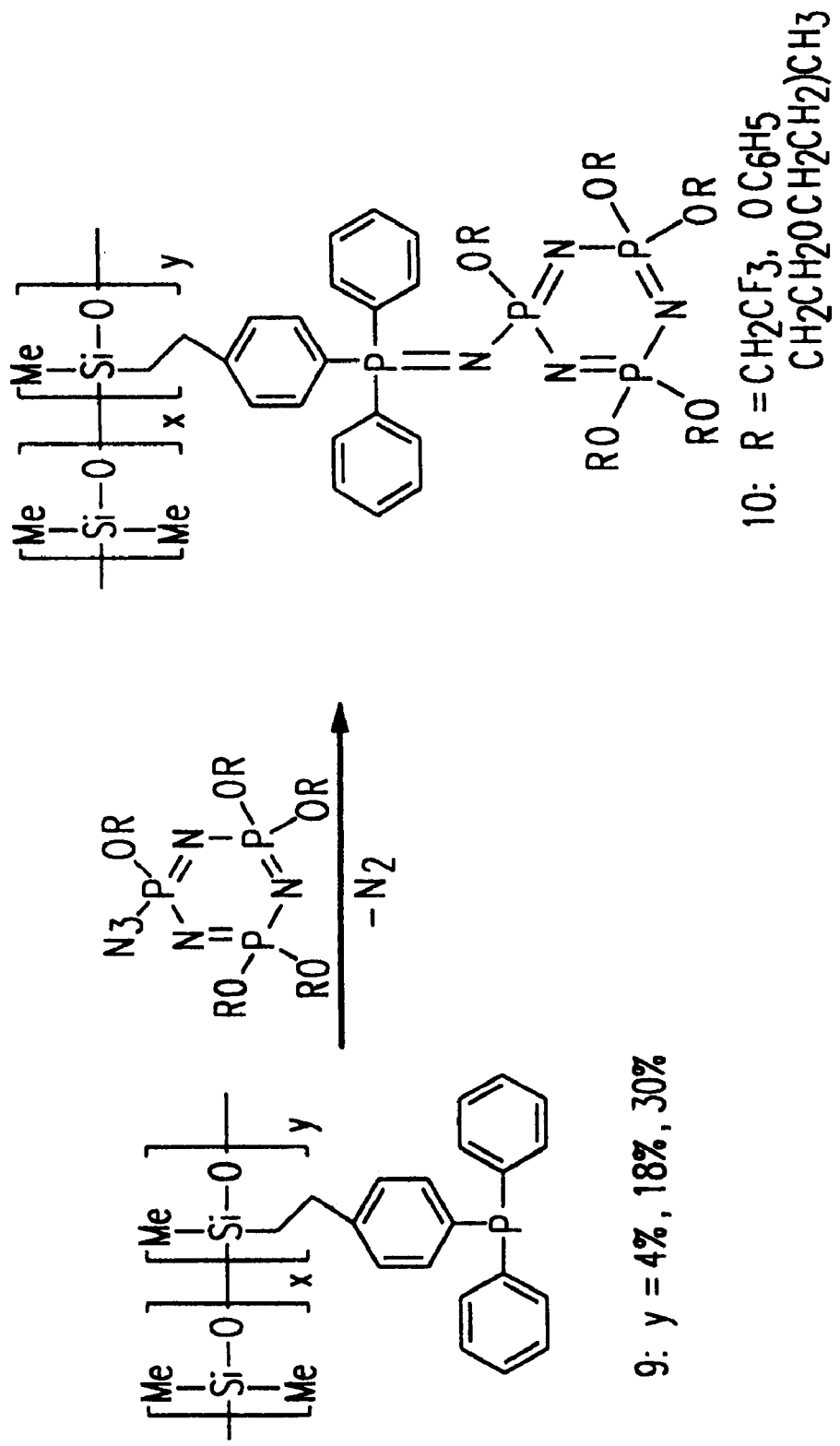
FIG. 12 shows a reaction scheme in which diphenyl-p-styrylphosphine is first coupled with polysiloxane, and then azidophosphazene trimer is covalently linked to the siloxane backbone via phosphinimine formation.

(a) Hydrosilylation Reaction Between Polydimethylsiloxane-co-Polyhydryomethylsiloxane and Diphenyl-p-styrylphosphine The reaction scheme is shown in FIG. 12. Diphenyl-p-styrylphosphine (Monomer 1) (1.49 g, 5.17 mmol) and PDMS-co-PHMS, (1.37 g, 18 mol % PHMS, 3.14 mmol PHMS, 71.48 average repeat unit, M$_w$=9171, PDI=1.7) were combined neat, degassed under vacuum, and then dissolved in 20 mL distilled toluene to form a solution. A catalytic amount (10 mg) of divinyldisiloxane:Pt catalyst was added to the solution, which was then allowed to reflux for 48 hrs. The progress of the reaction was monitored both by infrared spectroscopy, which showed the disappearance of the Si-H stretch at 2100 cm$^{-1}$, and by 31P NMR which showed the conversion of Monomer 1 (–5.1 ppm) to the hydrosilylated product. 9 (–6.0 ppm). Excess diphenyl-p-styrylphosphine was used to ensure the complete consumption of all the Si-H bonds. $^{31}$P NMR (THF): δ=–6.0 (s, 1P). M$_w$=18,000, PDI=2.00.

(b) Reaction Between N$_3$P$_3$(OCH$_2$CF$_3$)$_5$N$_3$ and the Phosphine Modified PDMS-co-PHMS (9)

Again see FIG. 12. N$_3$P$_3$(OCH$_2$CF$_3$)$_5$N$_3$ (3.48 g, 5.17 mmol) was added to the reaction mixture of 9. This mixture was heated to reflux in toluene (20 mL) for 24 hours. The polymer was purified by precipitations into hexanes (3x). The resultant white polymer was characterized by multinuclear NMR and GPC. $^1$H NMR (THF): δ=0 (m., [(Me$_3$)$_2$Si—O]$_x$—[H(Me$_3$)$_2$Si—O]$_y$), 0.09 (m, CH$_2$), 1.23 (m, CH$_2$), 2.35 (m, CH$_2$), 3.89 (s, OCH$_2$CF$_3$), 4.23 (s, OCH$_2$CF$_3$), 7.12–7.73 (bm, ArH); $^{31}$P NMR (THF): δ=10.15–11.92 (bm, 1P), 11.94–13.03 (bd, 1P), 17.19 (d, 1P), 18.11 (d, 2P). M$_w$=224298, multimodal due to the formation of aggregates in solution.

Modifications and variations of the present invention will be obvious to those of skill in the art from the foregoing detailed description. Such modifications and variations are intended to come within the scope of the following claims.

We claim:

1. A method for making a phosphazene-modified organic or siloxane polymer comprising
   (a) providing an organic or siloxane polymer comprising phosphine units, and
   (b) reacting the organic or siloxane polymer with a phosphazene azide compound under conditions wherein the phosphazene azide compound is bound to the phosphine units in the polymer, thereby producing the phosphazene-modified organic or siloxane polymer.

2. The method of claim 1 wherein the organic polymer of step (a) is produced by reacting a first monomer comprising phosphine with a second monomer via free radical or anionic polymerization techniques to produce the organic polymer comprising phosphine units.

3. The method of claim 2 wherein the first monomer and the second monomer have the same composition.

4. The method of claim 2 wherein the second monomer is a monomer polymerizable via free-radical or anionic polymerization techniques to form a polymer selected from the group consisting of polyolefins, polydienes, polyacrylics, polyethylenes, polyvinyl chlorides, polyisoprenes, polystyrenes, polycaprolactam. polymethylmethacrylates, and polypropylenes.

5. The method of claim 1 wherein the first monomer is diphenyl-p-styrylphosphine.

6. The method of claim 3 wherein the organic polymer of step (a) is poly(diphenyl-p-styrylphosphine).

7. The method of claim 1 wherein the siloxane polymer of step (a) is produced by reacting a monomer comprising phosphine with a hydrosilicone polymer via hydrosilylation synthetic techniques to produce the siloxane polymer comprising phosphine units.

8. The method of claim 7 wherein the hydrosilicone polymer is a copolymer having, the formula:

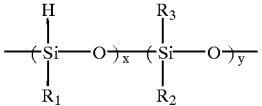

wherein R$_1$, R$_2$, and R$_3$ each are H or a linear, branched, or cyclic hydrocarbon, and wherein x is between 1% and 100%, and wherein y=(100–x)%.

9. The method of claim 8 wherein the copolymer is (methylhydrosiloxane)-(dimethylsiloxane).

10. The method of claim 1 wherein the phosphazene azide compound is a cyclotriphosphazene having a single azido side group.

11. The method of claim 1 wherein the phosphazene azide compound is a cyclotriphosphazene bearing multiple azido side groups.

12. The method of claim 1 wherein the phosphazene azide compound is a linear polyphosphazene bearing multiple azido side groups.

13. A phosphazene modified organic or siloxane polymer comprising
   (a) a backbone comprising an organic or siloxane polymer having phosphine units incorporated therein, and
   (b) phosphazene side chains coupled to the phosphine units.

14. The polymer of claim 13 wherein a phosphazene azide compound is reacted under conditions such that the phosphazene azide compound is bound to the phosphine units in the polymer.

15. The phosphazene modified organic polymer of claim 13 wherein the backbone comprising an organic polymer is produced by reacting a first monomer comprising phosphine with a second monomer via free radical or anionic polymerization techniques to produce the organic polymer having phosphine units.

16. The phosphazene modified organic polymer of claim 15 wherein the first monomer and the second monomer have the same composition.

17. The phosphazene modified organic polymer of claim 15 wherein the second monomer is a monomer polymerizable via free-radical or anionic polymerization techniques to form a polymer selected from the group consisting of polyolefins, polydienes, polyacrylics, polyethylenes, polyvinyl chlorides, polyisoprenes, polystyrenes, polycaprolactam, polymethylmethacrylates, and polypropylenes.

18. The phosphazene modified organic polymer of claim 15 where the second monomer is a methylmethacrylate or acrylate.

19. The phosphazene modified organic polymer of claim 15 wherein the second monomer is styrene.

20. The phosphazene modified organic polymer of claim 15 wherein the first monomer is diphenyl-p-styrylphosphine.

21. The phosphazene modified organic polymer of claim 16 wherein the organic polymer of the backbone is poly(diphenyl-p-styrylphosphine).

22. The phosphazene modified siloxane polymer of claim 13 wherein the backbone comprising a siloxane polymer is produced by reacting a monomer comprising phosphine with a hydrosilicone polymer via hydrosilylation synthetic techniques to produce the siloxane polymer having phosphine units.

23. The phosphazene modified siloxane polymer of claim 22 wherein the hydrosilicone polymer is a copolymer having the formula:

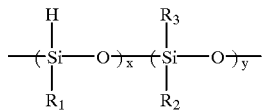

wherein $R^1$, $R_2$, and $R_3$ each are H or a linear, branched, or cyclic hydrocarbon, and wherein x is between 1% and 100%, and wherein y=(100−x)%.

24. The phosphazene modified siloxane polymer of claim 23 wherein the copolymer is (methylhydrosiloxane)-(dimethylsiloxane).

25. The polymer of claim 13 wherein the phosphazene azide compound is a cyclotriphosphazene having a single azido side group.

26. The polymer of claim 13 wherein the phosphazene azide compound is a cyclotriphosphazene bearing multiple azido side groups.

27. The polymer of claim 13 wherein the phosphazene azide compound is a linear polyphosphazene bearing multiple azido side groups.

28. The polymer of claim 13 having trimeric phosphazene rings linked to every repeating unit in the polymer backbone through a phosphinimine bond.

29. The polymer of claim 13 wherein the mole percentage of phosphinated monomer in the polymer is between about 1% and 100%.

30. An article of manufacture for use in fire retardance comprising a composition including a phosphazene modified organic or siloxane polymer which comprises
(a) a backbone comprising an organic or siloxane polymer having phosphine units incorporated therein, and
(b) phosphazene side chains coupled to the phosphine units.

* * * * *